(12) United States Patent  (10) Patent No.: US 11,207,675 B2
Yasuura et al.  (45) Date of Patent: Dec. 28, 2021

(54) TARGET SUBSTANCE DETECTION DEVICE AND TARGET SUBSTANCE DETECTION METHOD

(71) Applicant: NATIONAL INSTITUTE OF ADVANCED INDUSTRIAL SCIENCE AND TECHNOLOGY, Tokyo (JP)

(72) Inventors: Masato Yasuura, Ibaraki (JP); Makoto Fujimaki, Ibaraki (JP); Hiroki Ashiba, Ibaraki (JP); Takayuki Shima, Ibaraki (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 196 days.

(21) Appl. No.: 16/464,960

(22) PCT Filed: Jun. 22, 2017

(86) PCT No.: PCT/JP2017/023037
§ 371 (c)(1),
(2) Date: May 29, 2019

(87) PCT Pub. No.: WO2018/100779
PCT Pub. Date: Jun. 7, 2018

(65) Prior Publication Data
US 2020/0016588 A1 Jan. 16, 2020

(30) Foreign Application Priority Data
Nov. 30, 2016 (JP) .............................. JP2016-232382

(51) Int. Cl.
B01L 3/00 (2006.01)
G01N 21/01 (2006.01)
G01N 21/64 (2006.01)

(52) U.S. Cl.
CPC .............. *B01L 3/502* (2013.01); *G01N 21/01* (2013.01); *G01N 21/6428* (2013.01);
(Continued)

(58) Field of Classification Search
CPC ............. B01L 3/502; B01L 2300/0663; B01L 2300/0861; B01L 2300/168;
(Continued)

(56) References Cited

U.S. PATENT DOCUMENTS

2009/0321662 A1 12/2009 Ohtsuka
2011/0168918 A1 7/2011 Wimberger-Friedl et al.
(Continued)

FOREIGN PATENT DOCUMENTS

JP H04-102062 A 4/1992
JP H09-089774 A 4/1997
(Continued)

OTHER PUBLICATIONS

Extended Search Report issued in European Application No. 17 876 926.1-1020, dated Jul. 30, 2020.
(Continued)

*Primary Examiner* — Samuel P Siefke
*Assistant Examiner* — Oyeleye Alexander Alabi
(74) *Attorney, Agent, or Firm* — Michael Best & Friedrich LLP

(57) ABSTRACT

To detect a target substance accurately and effectively, a target substance detection device 1 includes: a liquid-sample introducing plate 2 formed from a light-transmissive plate having a surface on which a liquid sample including a target substance and magnetic particles forming a conjugate with
(Continued)

the target substance is introduced, and enabling propagating transmitted light of light irradiated from the rear face upward of the surface as propagated light; a rear face light irradiation unit 3 configured to be able to irradiate the liquid-sample introducing plate 2 with light from the rear face; a first magnetic field application unit 4 disposed on the side of the surface of the liquid-sample introducing plate 2, and configured to apply a magnetic field to move the conjugate in the liquid sample that is introduced on the surface of the liquid-sample introducing plate in the direction away from the liquid-sample introducing plate 2; and an optical-signal detection unit 5 disposed on the side of the surface of the liquid-sample introducing plate 2, and enabling detection of a change in optical signal based on the propagated light between before and after application of the magnetic field by the first magnetic field application unit 4.

5 Claims, 14 Drawing Sheets

(52) U.S. Cl.
CPC .............. *B01L 2300/0663* (2013.01); *B01L 2300/0861* (2013.01); *B01L 2300/168* (2013.01); *B01L 2400/043* (2013.01); *G01N 2021/6439* (2013.01)

(58) Field of Classification Search
CPC .............. B01L 2400/043; G01N 21/01; G01N 21/6428; G01N 2021/6439
See application file for complete search history.

(56) References Cited

U.S. PATENT DOCUMENTS

| | | | |
|---|---|---|---|
| 2012/0202194 A1* | 8/2012 | Evers | G01N 15/1434 |
| | | | 435/5 |
| 2012/0252111 A1 | 10/2012 | Tono et al. | |
| 2013/0088221 A1* | 4/2013 | Van Zon | G01N 27/72 |
| | | | 324/228 |
| 2013/0309779 A1 | 11/2013 | Kasai et al. | |
| 2013/0344590 A1 | 12/2013 | Konno et al. | |
| 2014/0302619 A1 | 10/2014 | Schleipen et al. | |

FOREIGN PATENT DOCUMENTS

| | | |
|---|---|---|
| JP | 2012-503769 A | 2/2012 |
| JP | 2012-215553 A | 11/2012 |
| JP | 2014-535060 A | 12/2014 |
| WO | 03/046511 A2 | 6/2003 |
| WO | WO-2003/046511 A2 | 6/2003 |
| WO | 2008/072156 A2 | 6/2008 |
| WO | WO-2008/072156 A2 | 6/2008 |
| WO | WO-2010/035204 A1 | 4/2010 |
| WO | 2011/036638 A1 | 3/2011 |
| WO | 2011/087916 A2 | 7/2011 |
| WO | WO-2011/087916 A2 | 7/2011 |
| WO | WO-2013/072806 A1 | 5/2013 |

OTHER PUBLICATIONS

The partial Supplement European search report mailed in European Patent Application No. 17876926.1, dated May 6, 2020.
International Search Report issued in Application No. PCT/JP2017/023037, dated Sep. 12, 2017.

* cited by examiner

TARGET SUBSTANCE DETECTION DEVICE AND TARGET SUBSTANCE DETECTION METHOD

TECHNICAL FIELD

The present invention relates to a target substance detection device configured to detect a target substance based on an optical-signal change when magnetic field moves the target substance in a liquid sample, and such a target substance detection method.

BACKGROUND ART

Recently methods have been developed to detect and determine the amount of a micro substance in liquid solution, particularly of biologically relevant substances, such as DNA, RNA, proteins, viruses, and bacteria. Examples of such a method include fluoroimmunoassay (FIA) and enzyme-linked immunosorbent assay (ELISA).

The FIA links an antibody specifically bound to a target substance, such as certain bacteria and viruses, with fluorochrome, and observes light-emission of the fluorochrome under a fluorescence microscope, so as to detect and determine the amount of the target substance.

The ELISA immobilizes such a target substance to a sensing plate through an antigen-antibody reaction, and binds the target substance to an enzyme-labeled antibody. The assay then adds a substrate having a property of changing the color with the enzyme, and detects and determines the amount of the target substance based on a color change.

Both of these methods are established assays and are widely used to detect biologically relevant substances. These methods, however, require multiple-stage of reaction processes and repeated washing process, and so needs a lot of time and effort to obtain the measurement result. More improved detection sensitivity also has been required.

To improve the detection sensitivity of a target substance of the above-described assays, a method of measuring a target substance using magnetic particles is proposed. For instance, Patent Document 1 discloses a detection method that attracts conjugates including a target substance and magnetic particles to a bottom of a vessel of a liquid sample, and immobilizes the conjugates to the bottom of the vessel through an antigen-antibody reaction between the antibody placed at the bottom and the conjugates.

Such a measurement method using magnetic particles improves the detection sensitivity due to the enrichment effect obtained by attracting the conjugates to a detection position by magnetic field. The method, however, may fail to distinguish between the optical signal based on the conjugates and a noise signal resulting from contaminants floating at the enriched detection position, contaminants adsorbed to the bottom of the vessel, scratches on the bottom of the vessel, or fluctuation of the output from a light source to emit light for detection, and so has a problem of low degree of detection accuracy. This problem is more obvious for the detection of micro substances as stated above.

To remove the noise signal from contaminants adsorbed to the bottom of the liquid-sample vessel, washing processing is required for every detection step to remove the contaminants. Such a method still has a problem of low effectivity of the detection.

PRIOR ART DOCUMENT

Patent Document

Patent Document 1: JP Hei 04-102062 A

SUMMARY OF THE INVENTION

Problems to be Solved by the Invention

To solve the above-stated problems of the conventional techniques, the present invention aims to provide a target substance detection device capable of detecting a target substance accurately and effectively and such a target substance detection method.

Means for Solving the Problems

Means for solving the above-stated problems is as follows.
<1> A target substance detection device includes:
a liquid-sample holding unit including a liquid-sample introducing plate including any one of: a light-transmissive plate having a surface on which a liquid sample including a target substance and magnetic particles forming a conjugate with the target substance is introduced, and capable of propagating transmitted light of light irradiated from a rear face or the surface to the face on an opposite of the irradiated face as propagated light; a reflective plate having a surface on which the liquid sample is introduced and capable of propagating reflected light of light irradiated from the surface upward of the surface as propagated light; and an introducing plate having a surface on which the liquid sample is introduced, wherein a surface of the liquid-sample introducing plate enables holding the liquid sample;
a light irradiation unit including any one of: when the liquid-sample introducing plate includes the light-transmissive plate, a rear face light irradiation unit configured to be able to irradiate the liquid-sample introducing plate with light from the rear face; when the liquid-sample introducing plate includes the light-transmissive plate or the reflective plate, a surface light irradiation unit configured to be able to irradiate the liquid-sample introducing plate with light from the surface; and when the liquid-sample introducing plate includes the introducing plate, a lateral face light irradiation unit configured to be able to irradiate the liquid sample held on the liquid-sample introducing plate with light from a lateral face of the liquid-sample introducing plate;
a magnetic field application unit including any one of: a first magnetic field application unit disposed on the side of the surface or the lateral face of the liquid-sample introducing plate, and configured to apply a magnetic field to move the conjugate in the liquid sample that is introduced on the surface of the liquid-sample introducing plate in any one of the directions including a direction having a vector component parallel to an in-plane direction of the surface of the liquid-sample introducing plate and a direction away from the liquid-sample introducing plate, or to change an orientation of the conjugate; and a second magnetic field application unit disposed on the side of the rear face of the liquid-sample introducing plate, and configured to apply a magnetic field to be able to draw the conjugate in the liquid sample that is introduced on the surface of the liquid-sample introducing plate toward the surface of the liquid-sample introducing plate, and being movable in a direction having a vector component parallel to the in-plane direction of the surface of the liquid-sample introducing plate while applying the magnetic field; and an optical-signal detection unit disposed on the side of the surface, the rear face or the lateral face of the liquid-sample introducing plate, and enabling detection of a change in optical signal based on the propagated light between before and after application of the magnetic field by the first magnetic field application unit or between before and after the movement of the second magnetic field application unit.

<2> The target substance detection device according to the said <1>, wherein the first magnetic field application unit has a through hole, and the optical-signal detection unit enables detection of an optical signal based on propagated light that is transmitted upward of the surface of the liquid-sample introducing plate through the through hole.

<3> The target substance detection device according to the said <1>, wherein the first magnetic field application unit has a through hole, and the surface light irradiation unit enables irradiation of the liquid-sample introducing plate with light from the surface through the through hole.

<4> The target substance detection device according to the said <1>, wherein the second magnetic field application unit has a through hole, and the rear face light irradiation unit enables irradiation of the liquid-sample introducing plate with light from the rear face through the through hole.

<5> The target substance detection device according to any one of the said <1> to <3>, further includes: when the magnetic field application unit includes the first magnetic field application unit, a third magnetic field application unit disposed on the side of the rear face of the liquid-sample introducing plate, and configured to apply a magnetic field to be able to draw the conjugate in the liquid sample that is introduced to the liquid-sample introducing plate toward the surface of the liquid-sample introducing plate.

<6> The target substance detection device according to the said <5>, wherein the third magnetic field application unit has a through hole, and the rear face light irradiation unit enables irradiation of the liquid-sample introducing plate with light from the rear face through the through hole.

<7> The target substance detection device according to any one of the said <1> to <6>, wherein the optical-signal detection unit enables acquisition of an image of a detection region on the surface of the liquid-sample introducing plate as a two-dimensional image.

<8> The target substance detection device according to any one of the said <1> to <7>, wherein the surface of the liquid-sample introducing plate is surface-treated with adsorption inhibitor that inhibits adsorption of the conjugate.

<9> The target substance detection device according to any one of the said <1> to <8>, wherein the liquid-sample holding unit has a channel capable of flowing liquid between the outside and a space on the surface of the liquid-sample introducing plate.

<10> A target substance detection method includes:

a liquid-sample introducing and holding step of introducing and holding a liquid sample including a target substance and magnetic particles making up a conjugate with the target substance on a surface of a liquid-sample introducing plate of a liquid-sample holding unit, wherein the liquid-sample holding unit includes the liquid-sample introducing plate including any one of a light-transmissive plate having a surface on which the liquid sample is introduced, and enabling propagating transmitted light of light irradiated from a rear face or the surface to the face on the opposite of the irradiated face as propagated light; a reflecting plate having a surface on which the liquid sample is introduced and enabling propagating reflected light of light irradiated from the surface upward of the surface as propagated light, and an introducing plate having a surface on which the liquid sample is introduced, and wherein the surface of the liquid-sample introducing plate enables to hold the liquid sample;

a light irradiation step including any one of when the liquid-sample introducing plate includes the light-transmissive plate, a rear face light irradiation step of irradiating the liquid-sample introducing plate with light from the rear face; when the liquid-sample introducing plate includes the light-transmissive plate or the reflective plate, a surface light irradiation step of irradiating the liquid-sample introducing plate with light from the surface; and when the liquid-sample introducing plate includes the introducing plate, a lateral face light irradiation step of irradiating the liquid sample held on the liquid-sample introducing plate with light from the lateral face of the liquid-sample introducing plate;

a conjugate moving step including any one of a first conjugate moving step of moving the conjugate in the liquid sample that is introduced to the surface of the liquid-sample introducing plate in any of the direction having a vector component parallel to an in-plane direction of the surface of the liquid-sample introducing plate and of the direction away from the liquid-sample introducing plate or changing the orientation of the conjugate by applying a magnetic field; and a second conjugate moving step of drawing the conjugate in the liquid sample introduced to the surface of the liquid-sample introducing plate by applying a magnetic field from the magnetic field application unit disposed on the side of the rear face of the liquid-sample introducing plate toward the surface of the liquid-sample introducing plate and moving the magnetic field application unit in the direction having a vector component parallel to an in-plane direction of the surface of the liquid-sample introducing plate while applying the magnetic field to move the conjugate or change the orientation of the conjugate in accordance with the movement of the magnetic field application unit; and an optical-signal detection step of detecting a change in optical signal based on the propagated light between before and after application of the magnetic field in the first conjugate moving step or between before and after movement of the magnetic field application unit in the second conjugate moving step.

<11> The target substance detection method according to the said <10>, wherein the conjugate includes a weight substance that promotes gravitational sedimentation.

<12> The target substance detection method according to the said <10>, including a conjugate drawing step when the conjugate moving step is the first conjugate moving step, the conjugate drawing step following the liquid-sample introducing and holding step, and being performed before the conjugate moving step, and drawing the entire or a part of the conjugate in the liquid sample toward the surface of the liquid-sample introducing plate by applying a drawing magnetic field.

<13> The target substance detection method according to any one of the said <10> to <12>, wherein the conjugate includes two or more magnetic particles bonding with one target substance.

<14> The target substance detection method according to any one of the said <10> to <13>, wherein the conjugate includes a labeled substance, and when the labeled substance is irradiated with propagated light, the labeled substance emits an optical signal that is distinguishable from an optical signal of transmitted light after the propagated light transmits the liquid sample.

Advantageous Effect of the Invention

The present invention solves the above-stated problems of the conventional techniques and provides a target substance detection device capable of detecting a target substance accurately and effectively and such a target substance detection method.

Figure 1:
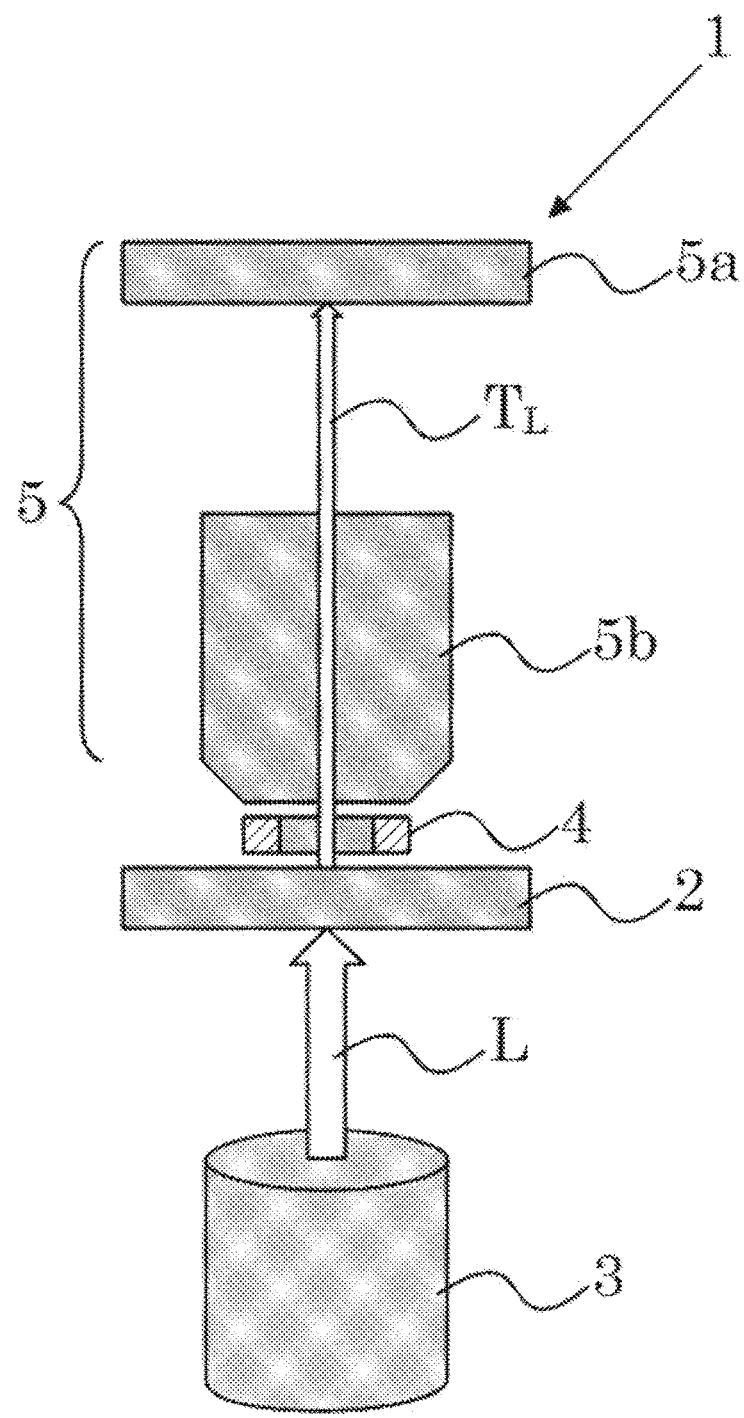
FIG. 1 describes a target substance detection device according to a first embodiment.

MODE FOR CARRYING OUT THE INVENTION (Target Substance Detection Device)

A target substance detection device of the present invention includes a liquid-sample holding unit, a light irradiation unit, a magnetic field application unit, and an optical-signal detection unit, and includes other units as needed.

<Liquid-Sample Holding Unit>

The liquid-sample holding unit includes a liquid-sample introducing plate and holds a liquid sample on the surface of the liquid-sample introducing plate.

—Liquid Sample—

The liquid sample at least includes a target substance and magnetic particles, and includes a labeled substance and a weight substance as needed.

Specific examples of the liquid sample include, for example, blood, saliva, urine, chemical liquid, environmental water, water supply and sewage, beverages, homogenized solution of foods, wiping liquid, solution containing a solid sample, such as powder, dissolved in solvent, such as water, and gas-phase concentrated solution containing trapped gas and particles in the gas phase. Specific examples of the target substances include, for example, DNA, RNA, proteins, viruses, bacteria and contaminated substances.

The magnetic particles are not limited especially as long as the particles form conjugates with the target substance and have such a property, and can be selected as needed depending on the purpose. For instance, well-known magnetic beads may be used for the magnetic particles.

A method for binding the magnetic particles with the target substance is not limited especially, and can be selected as needed depending on the purpose. Examples of the method include well-known binding methods, such as physical adsorption, antigen-antibody reaction, DNA hybridization, biotin-avidin bond, chelate bond, and amino bond. Examples of the binding method by physical adsorption include a method of binding the magnetic particles with the target substance using an electrostatic bonding force, such as hydrogen bond.

Advantageously such a binding method by physical adsorption is easy for operation because no pretreatment for the magnetic particles is required. Magnetic particles, however, do not adsorb only to the target substance specifically, and may bond with contaminants other than the target substance in the liquid sample. If the contaminants emit an optical signal similar to the target substance, the target substance cannot be distinguished from the contaminants. Preferable methods for binding magnetic particles with a target substance therefore involve pretreatment for the magnetic particles, and then specifically bind the target substance with the magnetic particles by the binding methods, such as antigen-antibody reaction, DNA hybridization, biotin-avidin bond, chelate bond, and amino bond.

The labeled substance bonds with the conjugates via the target substance and is irradiated with propagated light to emit an optical signal that is distinguishable from an optical signal (background signal) of the propagated light after transmitting and reflected from the liquid sample. Such a labeled substance is particularly effectively used when the target substance emits a very weak optical signal.

The labeled substance is not limited especially as long as the substance has such a property, and can be selected as needed depending on the purpose. Examples of the labeled substance include well-known fluorescence substances, such as fluorescent dye and quantum dots, light-scattering substances, such as nanoparticles including polystyrene beads and silica beads, and light-absorbing substances, such as gold nanoparticles.

A method for binding a target substance with a labeled substance is not limited especially, and can be selected as needed depending on the purpose. Examples of the method include well-known binding methods, such as physical adsorption, antigen-antibody reaction, DNA hybridization, biotin-avidin bond, chelate bond, and amino bond. When dye is used for the labeled substance, dying of the target substance with the die also is an effective method to bind the labeled substance with the target substance. Examples of the binding method by physical adsorption include a method of binding a labeled substance with a target substance using an electrostatic bonding force, such as hydrogen bond.

Among these binding methods, preferable methods specifically bind the target substance with the labeled substance through antigen-antibody reaction, DNA hybridization, biotin-avidin bond, chelate bond, amino bond and the like to avoid the bonding of the labeled substance with contaminants.

When both of the magnetic particles and the labeled substance bond with the target substance for detection, any one of these bonds preferably is a specific bond with the target substance. This is because, if both of the bonds occur in a non-specific manner, both of the magnetic particles and the labeled substance may bond with contaminants. This may cause a failure of distinguishing the target substance bonding with both of the magnetic particles and the labeled substance from the contaminants bonding with the magnetic particles and the labeled substance.

Preferably the magnetic particles, which issue an optical signal distinguishable from the background signal, such as fluorescence and scattering light, are used so as to double as the labeled substance, because this may omit the procedure of binding with the labeled substance.

The magnetic particles of such a type include ferrite particles that are surface-modified with organic polymer and having the diameter of 100 nm or more. Preferably the magnetic particles of such a type are used so that each conjugate has two or more of the magnetic particles binding with one of the target substance. Such a conjugate may be obtained by adjusting the number of the magnetic particles introduced into the liquid sample. Such binding of two or more of the magnetic particles with one of the target substance yields an optical signal that is more highly distinguishable from the background signal than in the binding of one of the magnetic particles with one of the target substance.

Although the number of the target substance in the liquid sample is unknown before the detection, the excessive amount of the magnetic particles may be introduced while considering the number of the target substance that is assumed from experience, so as to bind two or more of the magnetic particles with one of the target substance. The magnetic particles may be introduced to the liquid sample a plurality of times, and detection may follow each introduction. When the number of intense optical signals generated as stated above is saturated, the introduction of the magnetic particles may stop. This enables binding of two or more of the magnetic particles with one of the target substance efficiently.

The weight substance bonds with the conjugates via the target substance and promotes gravitational sedimentation of the conjugates. The weight substance is particularly effectively used when the conjugates have small specific gravity.

The weight substance is not limited especially as long as the weight substance has the property as stated above, and can be selected as needed depending on the purpose. Examples of the weight substance include well-known gold nanoparticles and the like.

A method for binding a target substance with a weight substance is not limited especially, and can be selected as needed depending on the purpose. Examples of the method include well-known binding methods, such as physical adsorption, antigen-antibody reaction, DNA hybridization, biotin-avidin bond, chelate bond, and amino bond. Examples of the binding method by physical adsorption include a method of binding a weight substance with a target substance using an electrostatic bonding force, such as hydrogen bond.

Among these binding methods, it is preferable to bind the target substance with the weight substance specifically through the antigen-antibody reaction, the DNA hybridization, the biotin-avidin bond, the chelate bond, the amino bond and the like to avoid the bonding of the weight substance with contaminants.

—Liquid-Sample Introducing Plate—

The liquid-sample introducing plate may include any one of a light-transmissive plate having a surface on which the liquid sample is introduced, and enabling transmission of light irradiated from a rear face or the surface so that the light propagates through the light-transmissive plate to the face on the opposite of the irradiated face as the propagated light; a reflective plate having a surface on which the liquid sample is introduced and enabling reflection of light irradiated from the surface so that the light propagates upward of the surface as the propagated light; and an introducing plate having a surface on which the liquid sample is introduced.

The light-transmissive plate is not limited especially, and can be selected as needed depending on the purpose. For instance, well-known light-transmissive plates can be used, such as a glass plate and a plastic plate used for an observation stage of a well-known transmission-type microscope.

The reflective plate is not limited especially, and can be selected as needed depending on the purpose. For instance, well-known reflective plates can be used, such as a glass plate, a plastic plate and a metal plate, used for an observation stage of a well-known vertical illumination type microscope.

The introducing plate is not limited especially, and can be selected as needed depending on the purpose. For instance, well-known plate members, including the light-transmissive plate and the reflective plate, may be used to introduce the liquid sample.

The propagated light typically does not include near-field light that rapidly attenuates at a position a few hundreds nm to a few μm away from the generation source. This description also means that the propagated light does not include such near-field light, and means the light that does not rapidly attenuate at a position a few hundreds nm to a few μm away from the surface of the liquid-sample introducing plate.

The liquid-sample introducing plate is not limited especially, and can be selected as needed depending on the purpose. Preferably the surface of the liquid-sample introducing plate is surface-treated with adsorption inhibitor that inhibits the adsorption of the conjugates. Such a surface treatment inhibits the adsorption of the conjugates to the surface of the liquid-sample introducing plate, and so assists the movement of the conjugates by the magnetic field application unit.

The adsorption inhibitor is not limited especially, and can be selected as needed from well-known adsorption inhibitors depending on the types of substances of the conjugate.

In one example, when the target substance is protein, the surface treatment may be well-known blocking methods to suppress adsorption of proteins. The blocking method is not limited especially, and examples of the blocking method include a method using polyethyleneglycol, a method using ethanolamine and a method using skim milk.

The structure of the liquid-sample holding unit is not limited especially, and can be selected as needed depending on the purpose. For instance, the liquid-sample holding unit may be the liquid-sample introducing sample plate itself. Another structure may include a plate-like light-transmissive member, such as a cover glass, and the liquid-sample introducing plate that are configured to sandwich the liquid sample between them, so as to hold the liquid layer of the liquid sample on the surface of the liquid-sample introducing plate.

Another structure of the liquid-sample holding unit may include a liquid cell like a square-shaped container having the liquid-sample introducing plate at the bottom.

The liquid-sample holding unit may have a plurality of subdivided regions on the surface of one liquid-sample introducing plate for multi-channeling.

Preferably the liquid-sample holding unit has a channel capable of flowing liquid between the outside and the space on the surface of the liquid-sample introducing plate.

Such a target substance detection device enables detection of a target substance without considering contaminants adsorbed to the liquid-sample introducing plate, and so enables the following detection without washing the liquid-sample introducing plate after each detection step. Such a target substance detection device, which has the channel in the liquid-sample holding unit, enables more efficient detection process because the liquid sample can be changed simply by introducing or discharging the liquid sample via the channel before the following detection.

In this description "washing process" means physical polishing or peeling with chemical agent of contaminants adsorbed to the surface of the liquid-sample introducing plate or removal of the contaminants by dissolution, and does not include rinsing with water during changing of the liquid sample.

<Light Irradiation Unit>

The light irradiation unit includes any one of a rear face light irradiation unit, a surface light irradiation unit, and a lateral-face light irradiation unit.

When the liquid-sample introducing plate is formed of the light-transmissive plate, the rear face light irradiation unit is configured to be able to irradiate the light from the rear face of the liquid-sample introducing plate.

The structure of the rear face light irradiation unit is not limited especially, and can be selected as needed depending on the purpose. For instance, this can be configured like a well-known light-irradiation unit in a well-known transmission-type microscope.

When the liquid-sample introducing plate is formed of the light-transmissive plate or the reflective plate, the surface light irradiation unit is configured to be able to irradiate the light from the surface of the liquid-sample introducing plate.

The structure of the surface light irradiation unit is not limited especially, and can be selected as needed depending on the purpose. For instance, when the liquid-sample introducing plate includes the reflective plate, the structure may be similar to a well-known light-irradiation unit in a well-known vertical illumination type microscope. When the liquid-sample introducing plate includes the light-transmissive plate, the structure may be similar to a well-known light-irradiation unit in a well-known transmission-type microscope.

When the liquid-sample introducing plate is formed of the introducing plate, the lateral face light irradiation unit is configured to be able to irradiate the liquid sample held on the liquid-sample introducing plate with light from the lateral face of the liquid-sample introducing plate.

The structure of the lateral face light irradiation unit is not limited especially, and can be selected as needed depending on the purpose. For instance, the structure may be similar to a well-known light-irradiation unit.

The light source for the rear face light irradiation unit, the surface light irradiation unit and the lateral face light irradiation unit is not limited especially, and can be selected as needed depending on the purpose. For instance, well-known light-emitting devices, such as lamps, LED devices, laser irradiation devices, can be used. The light source may be selected depending on the purpose. For instance, an excitation light source may be selected to detect light emission from the labeled substance, such as fluorescence.

Optical elements other than the light source of the rear face light irradiation unit, the surface light irradiation unit and the lateral face light irradiation unit also are not limited especially. These optical elements may be well-known optical elements as needed depending on the purpose.

<Magnetic Field Application Unit>

The magnetic field application unit includes any one of the following first magnetic field application unit and second magnetic field application unit. Both of the first magnetic field application unit and the second magnetic field application unit play a role of moving the conjugates introduced to the surface of the liquid-sample introducing unit and of changing the orientation of such conjugates. The target substance detection device detects a target substance based on a movement of the conjugates.

The term "movement" means the movement of the conjugates and a change in orientation of the conjugates.

—First Magnetic Field Application Unit—

The first magnetic field application unit is disposed on the side of the surface or the lateral face of the liquid-sample introducing plate. The first magnetic field application unit applies a magnetic field to move the conjugates in the liquid sample that are introduced on the surface of the liquid-sample introducing plate in any one of the directions including the direction having a vector component parallel to the in-plane direction of the surface of the liquid-sample introducing plate and the direction away from the liquid-sample introducing plate, or to change the orientation of the conjugates.

The first magnetic field application unit is not limited especially as long as it is the member as stated above, and can be selected as needed depending on the purpose. For instance, the first magnetic field application unit may include a well-known electromagnet or permanent magnet. When the permanent magnet is used, the first magnetic field application unit may be configured so that a movement member holding the permanent magnet is controlled to move between a near position where the magnetic field by the permanent magnet exerts the surface of the liquid-sample introducing plate and an away position where the magnetic field by the permanent magnet does not exert the surface of the liquid-sample introducing plate, so as to turn on and off of the application of the magnetic field to the surface of the liquid-sample introducing plate. A well-known magnetic shielding member may be controlled to have an open state to apply a magnetic field to the surface of the liquid-sample introducing plate and a shielding state not to apply the magnetic field to the surface of the liquid-sample introducing plate, so as to turn on and off of the application of the magnetic field to the surface of the liquid-sample introducing plate. When the electromagnet is used, excitation and demagnetization of the electromagnet may control the on-off of the application of the magnetic field to the surface of the liquid-sample introducing plate.

The first magnetic field application unit is not limited especially. Preferably the first magnetic field application unit has a through hole. Such a first magnetic field application unit allows the surface light irradiation unit to apply light from the surface of the liquid-sample introducing plate through the through hole. When the light irradiation unit is the surface light irradiation unit or the rear face light irradiation unit, such a first magnetic field application unit allows the optical-signal detection unit to detect an optical signal based on the propagated light that is propagated upward of the surface of the liquid-sample introducing plate through the through hole. Examples of the first magnetic field application unit having a through hole include an electromagnet including a coil without a core, a permanent magnet having a through hole, a U-letter shaped magnet, and a plurality of permanent magnets arranged along an arc.

—Second Magnetic Field Application Unit—

The second magnetic field application unit is disposed on the side of the rear face of the liquid-sample introducing plate. The second magnetic field application unit applies a magnetic field to draw the conjugates in the liquid sample that are introduced on the surface of the liquid-sample introducing plate toward the surface of the liquid-sample introducing plate, and is movable in the direction having a vector component parallel to the in-plane direction of the surface of the liquid-sample introducing plate while applying the magnetic field.

The second magnetic field application unit is not limited especially as long as it is the member as stated above, and can be selected as needed depending on the purpose. For instance, the second magnetic field application unit can include a well-known electromagnet or such a permanent magnet. For instance, the second magnetic field application unit holds the electromagnet or the permanent magnet on a slide member, and may be controlled about the movement to have an initial state where the electromagnet or the permanent magnet is located in the vicinity of a region (detection region) irradiated with the light from the light irradiation unit on the side of the surface or the rear face of the liquid-sample introducing plate, and a state where the electromagnet or the permanent magnet is shifted in the direction having a vector component parallel to the in-plane direction of the surface of the liquid-sample introducing plate. When the electromagnet is used, the electromagnet is continuously or intermittently energized during the control of the movement. During the control of the movement, the intensity of energizing may change.

A plurality of such electromagnets or permanent magnets may be disposed to control the application state of the magnetic field to each of the magnets, from which the same effect as that from the configuration holding the electromagnet or the permanent magnet on the slide member and controlling the movement can be obtained.

The second magnetic field application unit is not limited especially. Preferably the second magnetic field application unit has a through hole. Such a second magnetic field application unit allows the rear face light irradiation unit to apply light from the rear face of the liquid-sample introducing plate through the through hole. Examples of the second magnetic field application unit having a through hole include an electromagnet including a coil without a core, a permanent magnet having a through hole, a U-letter shaped magnet, and a plurality of permanent magnets arranged along an arc.

<Optical-Signal Detection Unit>

The optical-signal detection unit is disposed on the side of the surface, the rear face or the lateral face of the liquid-sample introducing plate. The optical-signal detection unit enables the detection of a change in optical signal based on the propagated light between before and after the application of the magnetic field by the first magnetic field application unit or between before and after the movement of the second magnetic field application unit.

Similarly to the optical signal acquired from a well-known transmission-type microscope or vertical illumination type microscope, the optical signal detected by the optical-signal detection unit based on the propagated light includes: an optical signal 1 of the light that is the transmitted light passing through or reflected from the liquid sample and is propagated upward of the surface of the liquid-sample introducing plate; an optical signal 2 that is generated when the propagated light is applied to the conjugates in the liquid sample and is distinguishable from the optical signal 1; an optical signal 3 that is generated when the propagated light is applied to contaminants in the liquid sample and is distinguishable from the optical signal 1; and an optical signal 4 that is generated when the propagated light is applied to scratches on the surface of the liquid-sample introducing plate or the contaminants adsorbed to the surface. This optical signal includes a noise signal as well, resulting from fluctuations in the output of the light source.

Although the optical signal 1 can be dealt with as a background signal, failure in distinguishing between the optical signals 2 to 4 and the noise signal may degrade the detection accuracy.

The target substance detection device moves the conjugates by the magnetic field application unit including the first magnetic field application unit and the second magnetic field application unit, and detects such a movement as a change of the optical signal based on the propagated light. In this way, the target substance detection device enables clear distinction between the optical signal 2 and the optical signals 3 and 4 or the noise signal.

That is, the optical signals 3 and 4 and the noise signal do not change due to the magnetic field applied between before and after the magnetic field applied by the first magnetic field application unit and before and after the movement of the second magnetic field application unit. On the contrary, the optical signal 2 results from the conjugates including the magnetic particles, and so changes between before and after the magnetic field applied by the first magnetic field application unit and before and after the movement of the second magnetic field application unit. Detection of a signal change of the optical signal based on the propagated light therefore enables accurate detection of the conjugates and accordingly the target substance making up the conjugates.

The changing optical signal 2 to be focused may have various forms depending on the types of the conjugates and the types of the optical systems of the target substance detection device. Specifically examples of the optical signal 2 include an optical signal based on the scattered light, the reflected light, the transmitted light in accordance with the phase difference and differential interference, light emission of the conjugates, such as fluorescence and phosphorescence, and light absorption of the conjugates, which are generated when the conjugates are irradiated with the propagated light. When the transmitted light in accordance with the phase difference and differential interference is detected as the optical signal 2, the liquid-sample holding unit, the light irradiation unit, and the optical-signal detection unit are configured as in the optical systems in a well-known phase-contrast microscope or a well-known differential interference microscope.

A change in the optical signal 2 includes an increase or decrease of the intensity, a phase change, a position shifting, the rotation of a shape, out of focus, and appearance/disappearance. This will be described later.

The optical-signal detection unit is not limited especially, and can be selected as needed depending on the purpose. The optical-signal detection unit may include a well-known photodetector, such as a photodiode and a photomultiplier and a well-known optical element, such as an objective lens.

The optical-signal detection unit is not limited especially, and is preferably configured to acquire the state of a detection region on the surface of the liquid-sample introducing plate as a two-dimensional image. Such a two-dimensional image enables easy acquisition of the positional information or the size information on the optical signals in the two-dimensional image that appear as light spots or dark spots. Comparison of the two-dimensional images before and after the movement of the conjugates enables clear distinction about whether the optical signal relates to the conjugates or about whether the optical signal relates to scratches on the surface of the liquid-sample introducing plate, the contaminants and the fluctuation in the output of the light source that do not relate to the conjugates. To obtain such two-dimensional image information, the optical-signal detection unit may include an imaging device.

The imaging device is not limited especially, and can be selected as needed depending on the purpose. Examples of the imaging device include well-known image sensors, such as a CCD image sensor and a CMOS image sensor.

A preferable method of detecting an optical signal by the optical-signal detection unit disposes the conjugates on the surface or in the vicinity of the surface of the liquid-sample introducing plate, and then places the surface of the liquid-sample introducing plate in an imaging range of the optical-signal detection unit. This is to avoid a failure of the detection of the conjugates outside of the imaging range of the optical-signal detection unit. The "imaging range" means a focal depth or the vicinity of the focal depth that is the range where an optical signal can be obtained.

Detection of the target substance includes detecting the presence or not of the target substance, detecting the amount of the target substance (to determine the quantity), and real-time observation of the presence of the target substance.

<Other Units>

The other units are not limited especially, and can be selected as needed depending on the purpose. The other units include a third magnetic field application unit and any units used in a well-known transmission-type microscope, a well-known vertical illumination type microscope and the like.

—Third Magnetic Field Application Unit—

The third magnetic field application unit is disposed on the side of the rear face of the liquid-sample introducing plate when the magnetic field application unit includes the first magnetic field application unit. The third magnetic field application unit applies a magnetic field to draw the conjugates in the liquid sample that are introduced to the liquid-sample introducing plate toward the surface of the liquid-sample introducing plate.

When the magnetic field application unit includes the second magnetic field application unit, the magnetic field applied draws the conjugates in the liquid sample to the surface of the liquid-sample introducing plate. The optical-signal detection unit therefore detects the optical signal while focusing on the surface or the vicinity of the surface of the liquid-sample introducing plate, so as to detect the movement of the conjugates drawn to the surface.

When the magnetic field application unit includes the first magnetic field application unit and when the optical-signal detection unit detects an optical signal while focusing on the surface or the vicinity of the surface of the liquid-sample introducing plate, the conjugates may not be always drawn to the surface of the liquid-sample introducing plate. Instead, the conjugates may float in the liquid layer of the liquid sample immediately after the liquid sample is introduced to the liquid-sample introducing plate. If the floating conjugates are outside of the imaging range where the optical-signal detection unit can detect the optical signals, the optical-signal detection unit may fail to detect the conjugates.

Such detection of the optical signals by the optical-signal detection unit while focusing on the surface or the vicinity of the surface of the liquid-sample introducing plate has to wait for gravitational sedimentation of the conjugates on the surface of the liquid-sample introducing plate after introducing the liquid sample to the liquid-sample introducing plate. The detection therefore takes a time for preparation. Especially when the conjugates have small specific gravity, the detection takes a longer time.

The third magnetic field application unit therefore applies a magnetic field to draw the conjugates floating in the liquid layer of the liquid sample to the surface of the liquid-sample introducing plate. This shortens the time for preparation of the detection and enables more efficient detection.

As another efficient method of shortening the time for gravitational sedimentation of the conjugates on the surface of the liquid-sample introducing plate without using the third magnetic field application unit, the conjugates may include the weight substance.

The third magnetic field application unit is not limited especially, and can be selected as needed depending on the purpose. For instance, the third magnetic field application unit may include a well-known electromagnet or permanent magnet.

The third magnetic field application unit is required to, after drawing the conjugates to the surface of the liquid-sample introducing plate, on-off control the application of the magnetic field that draws the conjugates so as not to interfere with the movement of the conjugates by the first magnetic field application unit. To this end, the configuration including the permanent magnet enables on-off control the application of the magnetic field by controlling the movement of a movable member holding the permanent magnet between a near state where the magnetic field by the permanent magnet exerts the liquid layer of the liquid sample and an away state where the magnetic field by the permanent magnet does not exert the liquid layer of the liquid-sample introducing plate. Alternatively a well-known magnetic shielding member may be controlled to have an open state to apply a magnetic field to conjugates to draw the conjugates to the surface and a shielding state not to apply such a magnetic field to the conjugates, so as to turn on and off of the application of the magnetic field. When the electromagnet is used, excitation and demagnetization of the electromagnet may control the on-off of the application of the magnetic field.

The third magnetic field application unit is not limited especially. Preferably the third magnetic field application unit has a through hole. Such a third magnetic field application unit allows the rear face light irradiation unit to apply light from the rear face of the liquid-sample introducing plate through the through hole. Examples of the third magnetic field application unit having a through hole include an electromagnet including a coil without a core, a permanent magnet having a through hole, a U-letter shaped magnet, a plurality of permanent magnets arranged along an arc and the like.

The configuration having such a third magnetic field application unit collects the conjugates in the detection region (irradiated with light from the light irradiation unit and generating the propagated light upward of the surface) on the surface of the liquid-sample introducing plate for enrichment, and enables more accurate detection of the target substance.

(Target Substance Detection Method)

A target substance detection method of the present invention includes a liquid-sample introducing and holding step, a light irradiation step, a conjugate moving step, and an optical-signal detection step, and includes other steps as needed.

<Liquid-Sample Introducing and Holding Step>

The liquid-sample introducing and holding step is a step of introducing and holding a liquid sample including a target substance and magnetic particles making up a conjugate with the target substance on a surface of a liquid-sample introducing plate of a liquid-sample holding unit, wherein the liquid-sample holding unit includes the liquid-sample introducing plate including any one of a light-transmissive plate having a surface on which the liquid sample is introduced, and enabling transmission of light irradiated from a rear face or the surface so that the light propagates through the light-transmissive plate to the face on the opposite of the irradiated face as propagated light; a reflecting plate having a surface on which the liquid sample is introduced and enables reflection of light irradiated from the surface so that the light propagates upward of the surface as propagated light; and an introducing plate having a surface on which the liquid sample is introduced, and wherein the surface of the liquid-sample introducing plate enables to hold the liquid sample.

As the liquid sample, the liquid sample described for the above target substance detection device may be used.

As the liquid-sample introducing plate, the liquid-sample introducing plate described for the above target substance detection device may be used.

In a pre-step of the liquid-sample introducing and holding step, the liquid sample is prepared by mixing with the magnetic particles, a labeled substance and a weight substance as needed. Typically magnetic particles, a labeled substance and a weight substance are dispersed in solution for storage or are stored in the powder form, and they are added to the liquid sample for mixing before use.

A method for mixing of the liquid sample is not limited especially and can be selected as needed depending on the purpose. For instance, the method includes (1) after holding the liquid sample without the magnetic particles, the labeled substance and the weight substance added in the liquid sample at the liquid-sample holding unit, adding the magnetic particles, the labeled substance and the weight substance to the liquid sample for mixing, (2) after holding the magnetic particles, the labeled substance, and the weight substance at the liquid-sample holding unit, introducing the liquid sample without the magnetic particles, the labeled substance, and the weight substance added to the liquid-sample holding unit for mixing, and (3) before introducing to the liquid-sample holding unit, adding the magnetic particles, the labeled substance and the weight substance to the liquid sample that does not include the magnetic particles, the labeled substance and the weight substance for mixing (pre-mixing method).

Among these methods, the pre-mixing method of (3) collects the magnetic particles and the conjugates including the magnetic particles in the mixing vessel with a magnet via the mixing vessel and separates a part of the mixing solution while keeping these magnetic particles and conjugates in the vessel with the magnet so as not to fall from the vessel. This can suppress the mixing of contaminants in the liquid sample to be introduced into the liquid-sample holding unit and can enrich the conjugates in the liquid sample to be introduced into the liquid-sample holding unit. As a result, this method enables more accurate detection than in the method of (1) and (2).

This step may mix the target substance that has a solid form by drying, for example, with solution including the magnetic particles, the labeled substance and the weight substance dispersed so as to prepare the liquid sample.

<Light Irradiation Step>

The light irradiation step includes any one of: when the liquid-sample introducing plate is formed of the light-transmissive plate, a rear face light irradiation step of irradiating the liquid-sample introducing plate with light from the rear face; when the liquid-sample introducing plate is formed of the light-transmissive plate or the reflective plate, a surface light irradiation step of irradiating the liquid-sample introducing plate with light from the surface; and when the liquid-sample introducing plate is formed of the introducing plate, a lateral face light irradiation step of irradiating the liquid sample held on the liquid-sample introducing plate with light from the lateral face of the liquid-sample introducing plate.

The rear face light irradiation step may be implemented by the rear face light irradiation unit described for the above target substance detection device.

The surface light irradiation step may be implemented by the surface light irradiation unit described for the above target substance detection device.

The lateral face light irradiation step may be implemented by the lateral face light irradiation unit described for the above target substance detection device.

<Conjugate Moving Step>

The conjugate moving step includes any one of a first conjugate moving step of moving the conjugates in the liquid sample introduced to the surface of the liquid-sample introducing plate in any of the direction having a vector component parallel to an in-plane direction of the surface of the liquid-sample introducing plate and of the direction away from the liquid-sample introducing plate or changing the orientation of the conjugates by applying a magnetic field; and a second conjugate moving step of drawing the conjugates in the liquid sample introduced to the surface of the liquid-sample introducing plate by applying magnetic field from the magnetic field application unit disposed on the side of the rear face of the liquid-sample introducing plate to the surface of the liquid-sample introducing plate and moving the magnetic field application unit in the direction having a vector component parallel to an in-plane direction of the surface of the liquid-sample introducing plate while applying the magnetic field to move the conjugates or change the orientation of the conjugates in accordance with the movement of the magnetic field application unit.

The first conjugate moving step may be implemented by the first magnetic field application unit described for the above target substance detection device.

The second conjugate moving step may be implemented by the second magnetic field application unit described for the above target substance detection device.

The first conjugate moving step and the second conjugate moving step may be performed repeatedly while inserting the optical-signal detection step, and this can increase the detection accuracy. The target substance detection device, which has both of the first magnetic field application unit and the second magnetic field application unit, may combine the first conjugate moving step and the second conjugate moving step.

In this conjugate moving step, the liquid-sample introducing plate may be moved in the direction having a vector component parallel to an in-plane direction of the surface of the liquid-sample introducing plate during the application of the magnetic field, from which similar effects may be obtained.

<Optical-Signal Detection Step>

The optical-signal detection step is a step of detecting a change in optical signal based on the propagated light between before and after the application of the magnetic field in the first conjugate moving step or between before and after the movement of the magnetic field application unit in the second conjugate moving step.

The optical-signal detection step may be implemented by the optical-signal detection unit described for the above target substance detection device.

<Other Steps>

The other steps are not limited especially, and can be selected as needed depending on the purpose. For instance, the other steps may include a conjugate drawing step.

—Conjugate Drawing Step—

The conjugate drawing step is performed when the conjugate moving step is the first conjugate moving step. This step follows the liquid-sample introducing and holding step, and is performed before the conjugate moving step, and draws the entire or a part of the conjugates in the liquid sample to the surface of the liquid-sample introducing plate by applying a drawing magnetic field.

When the conjugate moving step is implemented by the first conjugate moving step, and when the optical-signal detection step detects an optical signal while focusing on the surface or the vicinity of the surface of the liquid-sample introducing plate, the conjugates may not be always drawn to the surface of the liquid-sample introducing plate. Instead, the conjugates may float in the liquid layer of the liquid sample immediately after the liquid sample is introduced to the liquid-sample introducing plate. If the floating conjugates are outside of the imaging range where the optical-signal detection step can detect the optical signals, the optical-signal detection step may fail to detect the conjugates.

Such detection of the optical signals by the optical-signal detection step while focusing on the surface or the vicinity of the surface of the liquid-sample introducing plate has to wait for gravitational sedimentation of the conjugates on the surface of the liquid-sample introducing plate after introducing the liquid sample to the liquid-sample introducing plate. The detection therefore takes a time for preparation. Especially when the conjugates have small specific gravity, the detection takes a longer time.

When the conjugate moving step includes the first conjugate moving step, the method therefore preferably includes the conjugate drawing step to shorten the preparation for the detection and detect the conjugates more effectively.

The conjugate drawing step may be implemented by the third magnetic field application unit described for the above target substance detection device.

As another efficient method of shortening the time for gravitational sedimentation of the conjugates on the surface of the liquid-sample introducing plate without performing the conjugate drawing step, the conjugates may include the weight substance.

When the conjugate drawing step is performed and when the first conjugate moving step is performed by moving the conjugates in the direction away from the liquid-sample introducing plate, the method includes, but is not limited to, the following steps. That is, the conjugate drawing step, the conjugate moving step and the optical-signal detection step are preferably repeatedly a plurality of times performed in this order after the liquid-sample introducing and holding step (alternate application of magnetic field).

Such alternate application of magnetic field can increase the detection accuracy because this enables repeated detection of the optical signal from the same conjugate. The alternate application of magnetic field may be performed periodically, and a well-known lock-in amplifier may be applied to the frequency of the optical signal from the same conjugate to amplify the optical signal. This can improve the sensitivity of the detection.

Referring to the drawings, the following describes some embodiments of the present invention in details.

First Embodiment

Firstly referring to FIG. 1, the following describes a target substance detection device according to a first embodiment of the present invention. FIG. 1 describes the target substance detection device according to the first embodiment.

As shown in FIG. 1, a target substance detection device 1 is configured like a well-known transmission type microscope, and includes a liquid-sample introducing plate 2, a light irradiation unit 3, a first magnetic field application unit 4, and an optical-signal detection unit 5 including an imaging device 5a and an objective lens 5b. In one example, the imaging device 5a includes, for example, a well-known CCD image sensor to acquire a two-dimensional image.

The liquid-sample introducing plate 2 has a surface, to which a liquid sample including a target substance and magnetic particles forming the conjugate with the target substance is introduced. The liquid-sample introducing plate 2 includes a light-transmissive plate that propagates transmitted light $T_L$ of the light L irradiated from the rear face upward of the surface as propagated light. The liquid-sample introducing plate 2 itself makes up the liquid-sample holding unit, and after the liquid sample is introduced to the surface, a cover glass, for example, is placed so as to cover the liquid sample. In this way the liquid-sample introducing plate holds the liquid sample.

The light irradiation unit 3 makes up the rear face light irradiation unit that applies the light L from the rear face of the liquid-sample introducing plate 2.

The first magnetic field application unit 4 is disposed on the side of the surface of the liquid-sample introducing plate 2, and is configured to apply a magnetic field so as to move the conjugates in the liquid sample that are introduced onto the surface of the liquid-sample introducing plate 2 in the direction away from the liquid-sample introducing plate 2. The first magnetic field application unit 4 includes an annular electromagnet having a through hole at the center, and the optical-signal detection unit 5 detects an optical signal based on the transmitted light $T_L$ of the light L irradiated from the light irradiation unit 3 through the through hole.

The optical-signal detection unit 5 is disposed on the side of the surface of the liquid-sample introducing plate 2, and detects a change in optical signal based on the propagated light between before and after the application of the magnetic field by the first magnetic field application unit 4.

The liquid-sample introducing plate 2, the light irradiation unit 3 and the optical-signal detection unit 5 (imaging device 5a and the objective lens 5b) may be configured like a well-known transmission type microscope.

Such a target substance detection device 1 firstly introduces a liquid sample to the surface of the liquid-sample introducing plate 2 and holds the liquid sample on the surface (liquid-sample introducing and holding step).

Next, after gravitational sedimentation of the conjugates floating in the liquid layer of the liquid sample on the surface of the liquid-sample introducing plate 2, the target substance detection device applies the light L from the rear face of the liquid-sample introducing plate 2 (light irradiation step), and adjusts the objective lens 5b so that the surface or the vicinity of the surface is within the imaging range to acquire an optical signal on the surface with the imaging device 5a (optical-signal detection step).

Figure 2:
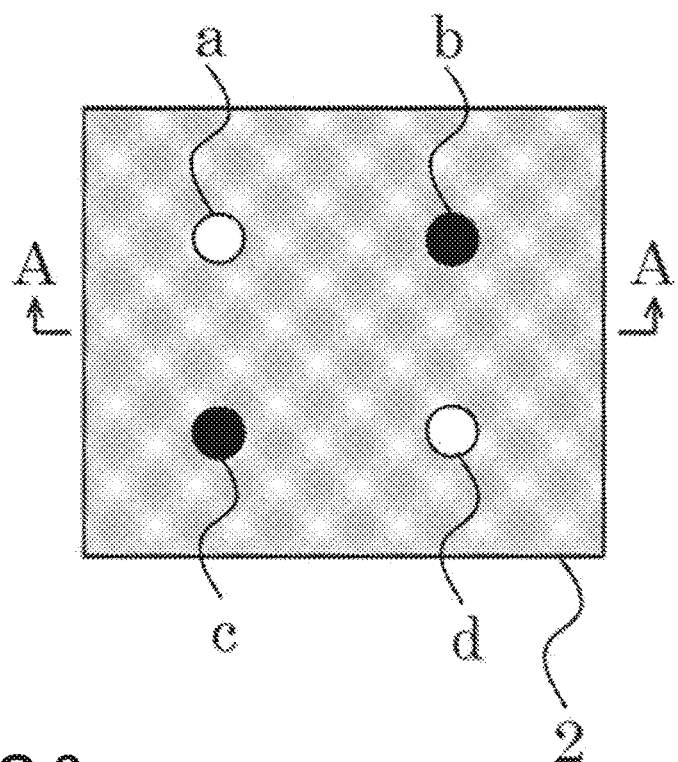
FIG. 2 is Drawing (1) schematically showing the surface of the liquid-sample introducing plate in the field of view that is observed with an imaging device.

FIG. 2 schematically shows the surface of the liquid-sample introducing plate 2 in the field of view that is observed with the imaging device 5a.

As shown in FIG. 2, four optical signals a to d are observable on the surface of the liquid-sample introducing plate 2 in the field of view, and these optical signals are distinguishable from the optical signal (background signal) of the transmitted light of the liquid sample that is propagated upward of the surface of the liquid-sample introducing plate 2 as the propagate light because of a difference in contrast from the background signal. FIG. 2 shows the optical signals a and d that are observed as light spots and the optical signals b and c that are observed as dark spots.

Figure 3:
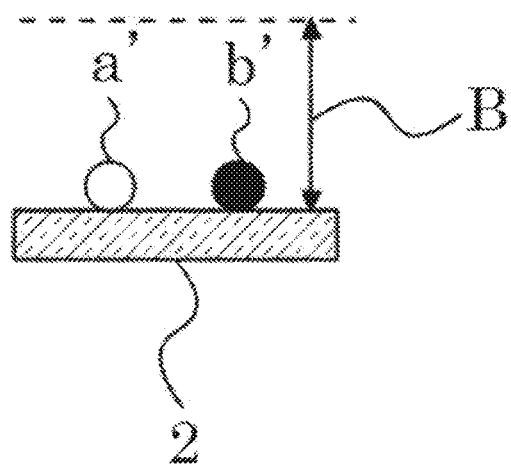
FIG. 3 is a cross-sectional view taken along the line A-A of FIG. 2.

FIG. 3 is a lateral view of the liquid-sample introducing plate 2 showing substance a' that generates the optical signal a and substance b' that generates the optical signal b. FIG. 3 is a cross-sectional view taken along the line A-A of FIG. 2. Arrow B in FIG. 3 indicates the imaging range where an optical signal can be obtained.

As shown in FIG. 3, the substance a' and the substance b' are gravitationally settled on the surface of the liquid-sample introducing plate 2.

Next the target substance detection device excites the electromagnet of the first magnetic field application unit 4 to apply a magnetic field to draw the conjugates in the liquid sample introduced to the surface of the liquid-sample introducing plate 2 toward the first magnetic field application unit 4, and move the conjugates in the direction away from the liquid-sample introducing plate 2 (first conjugate moving step).

Next, after moving the conjugates in the direction away from the liquid-sample introducing plate 2 while keeping the imaging range and the field of view, the target substance detection device acquires an optical signal on the surface of the liquid-sample introducing plate 2 with the imaging device 5a (optical-signal detection step).

Figure 4:
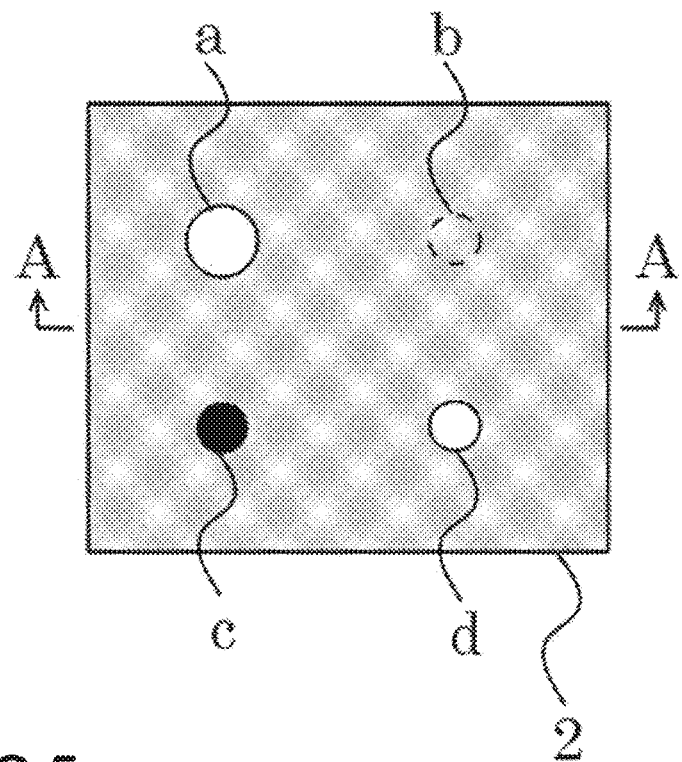
FIG. 4 is Drawing (1) schematically showing the surface of the liquid-sample introducing plate in the field of view that is observed with an imaging device after the conjugate moving step.

FIG. 4 schematically shows the surface of the liquid-sample introducing plate 2 in the field of view that is observed with the imaging device 5a after the first conjugate moving step.

As is understood from a comparison between FIG. 2 showing the surface before the first conjugate moving step and FIG. 4 showing the surface after the first conjugate moving step, the optical signals a and b change between before and after the first conjugate moving step, and the optical signals c and d do not change between before and after the first conjugate moving step.

This shows that the substances a' and b' that generate the optical signals a and b are the conjugates including the magnetic particles that are drawn by the first magnetic field application unit 4, and so include the target substance.

On the contrary, no change is observed for the optical signals c and d between before and after the first conjugate moving step, and so this shows that these optical signals are noise signals due to scratches on the surface of the liquid-sample introducing plate 2, contaminants adsorbed to or present on the surface, fluctuation of the output from the light source and the like.

Figure 5:
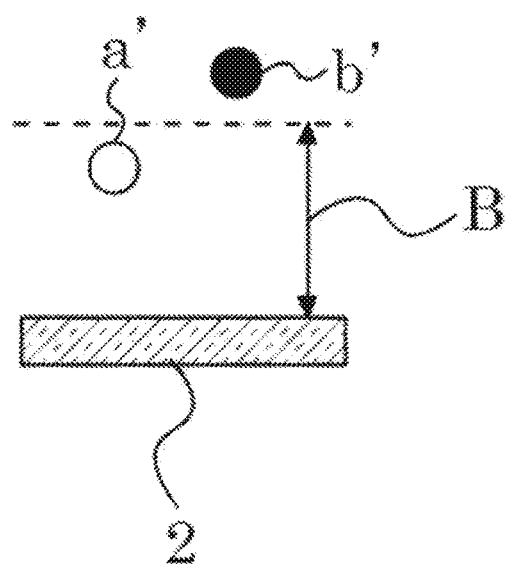
FIG. 5 is a cross-sectional view taken along the line A-A of FIG. 4.

FIG. 5 is a lateral view of the liquid-sample introducing plate 2 showing the substance a' that generates the optical signal a and the substance b' that generates the optical signal b after the first conjugate moving step. FIG. 5 is a cross-sectional view taken along the line A-A of FIG. 4. Arrow B in FIG. 5 indicates the imaging range where an optical signal can be obtained.

As shown in FIG. 5, the magnetic field applied by the first magnetic field application unit 4 moves the substance a' and the substance b' in the direction away from the liquid-sample introducing plate 2.

The optical signal a increases in size of the light spot after the first conjugate moving step (see FIG. 4). This is because, although the substance a' is still present in the imaging range of the optical-signal detection unit 5, the substance a' went out of focus because the focus is at the surface of the liquid-sample introducing plate 2 before the first conjugate moving step, and so the size of the light spot observed increases (see FIG. 5).

On the contrary, the optical signal b disappears after the first conjugate moving step (see FIG. 4). This is because the substance b' moved to the outside of the imaging range of the optical-signal detection unit 5 (see FIG. 5).

The optical signal a is observed as a light spot (see FIG. 2 and FIG. 4). This is because the substance a' is irradiated with the propagated light and emits light, such as scattering light and fluorescence.

The optical signal b is observed as a dark spot (see FIG. 2 and FIG. 4). This is because when irradiated with the propagated light, the substance b' emits transmitted light that has a smaller intensity than that of the propagated light due to the light absorption or the light reflection.

As stated above, the target substance detection device 1 clearly distinguishes an optical signal based on the target substance from noise signals due to scratches on the surface of the liquid-sample introducing plate 2, contaminants adsorbed to or present on the surface, fluctuation of the output from the light source and the like, and so enables accurate detection of the target substance. The target substance detection device allows detection of the target substance irrespective of contaminants adsorbed to the surface of the liquid-sample introducing plate 2, if any, and so does not require the washing process for the liquid-sample introducing plate 2 for every detection step. In this way the target substance detection device enables efficient detection. The target substance detection device deals with various types of optical signals that are generated based on scattered light, reflected light, light emission, such as fluorescence, and light absorption, as signals to be distinguished, and so will be applied in a wide range of fields. The target substance detection device deals with the phenomena of a change in optical signal including out-of-focus as well as disappearance of the optical signal, and so can obtain a change of the optical signal clearly.

Figure 6:
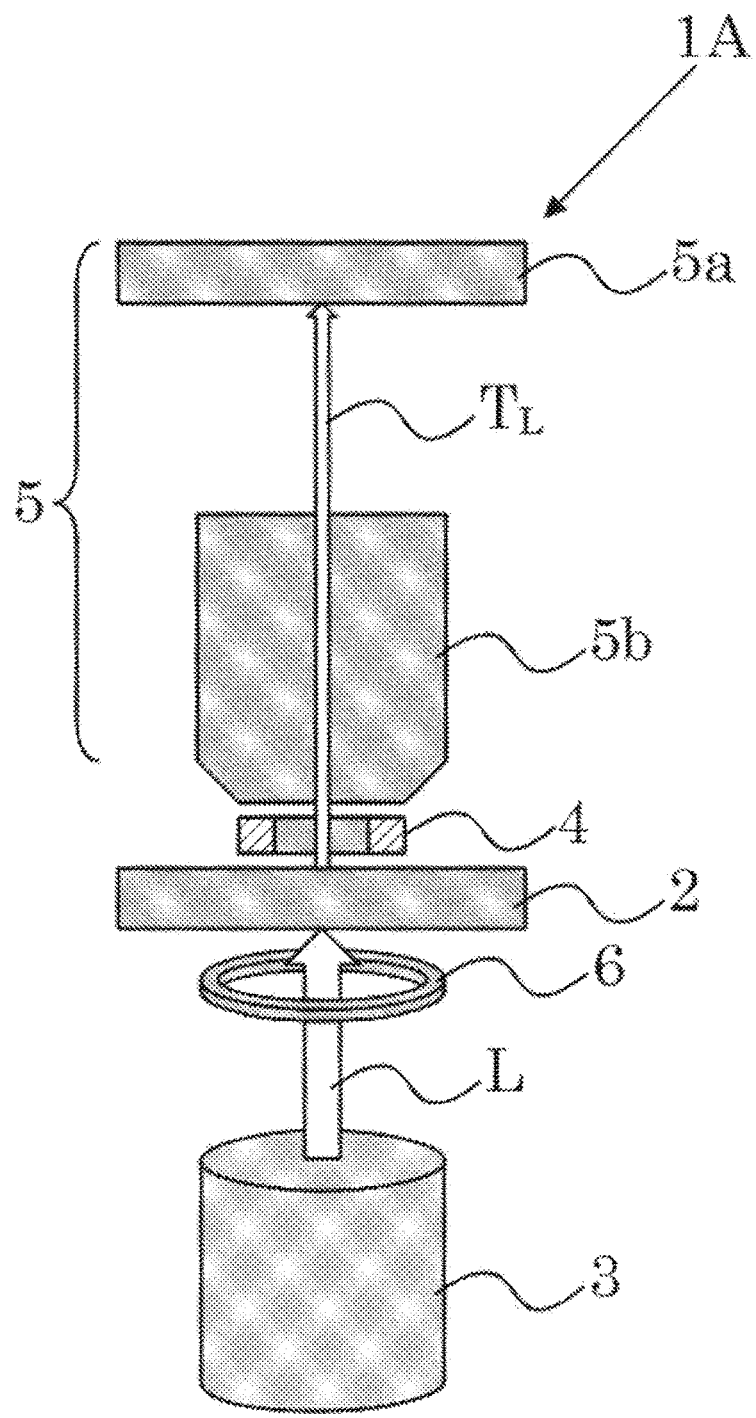
FIG. 6 describes a target substance detection device according to a first modified example of the first embodiment.

Next referring to FIG. 6, the following describes a target substance detection device according to a first modified example of the target substance detection device of the first embodiment. FIG. 6 describes the target substance detection device according to the first modified example.

As shown in FIG. 6, the target substance detection device 1A according to the first modified example includes a third magnetic field application unit 6 in addition to the target substance detection device 1 of the first embodiment. This target substance detection device has a similar structure to the target substance detection device 1 according to the first embodiment in the other respects, and so the descriptions are omitted.

The third magnetic field application unit 6 is disposed on the side of the rear face of the liquid-sample introducing plate 2 and applies a magnetic field to draw the conjugates in the liquid sample that are introduced to the liquid-sample introducing plate 2 toward the surface of the liquid-sample introducing plate 2. The third magnetic field application unit 6 in this example includes an annular electromagnet having a through hole, and so the light irradiation unit 3 applies light from the rear face of the liquid-sample introducing plate 2 via the through hole.

Similarly to the target substance detection device 1, after the liquid-sample introducing and holding step and before the conjugate moving step, the third magnetic field application unit 6 in the target substance detection device 1A applies a drawing magnetic field to draw the entire or a part of the conjugates in the liquid sample toward the surface of the liquid-sample introducing plate 2 without waiting for gravitational sedimentation of the floating conjugates in the liquid layer of the liquid sample on the surface of the liquid-sample introducing plate 2 (conjugate drawing step).

In addition to the advantageous effect of the target substance detection device 1, this target substance detection device 1A shortens the time required for the detection and so enables more efficient detection of the target substance.

Figure 7:
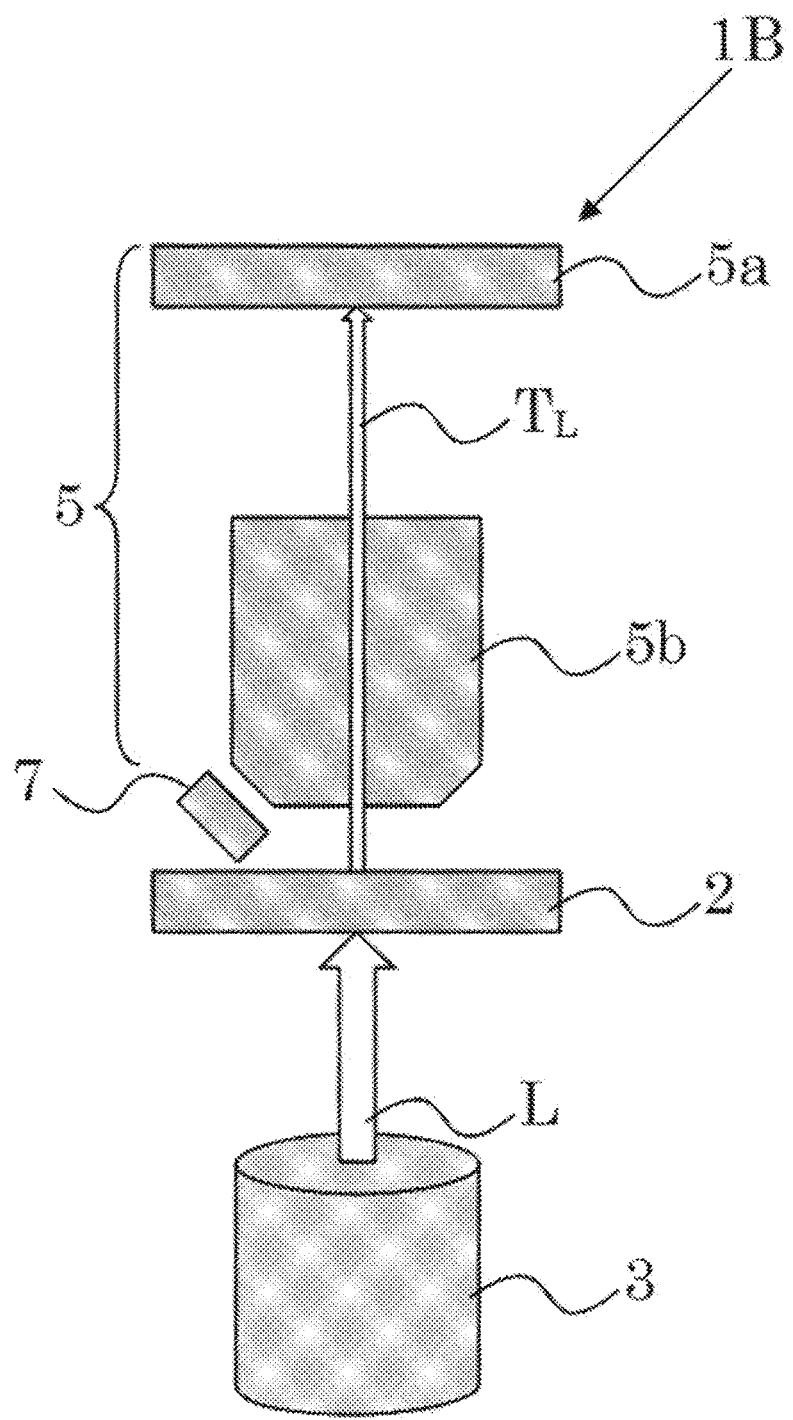
FIG. 7 describes a target substance detection device according to a second modified example of the first embodiment.

Next referring to FIG. 7, the following describes a target substance detection device according to a second modified example of the target substance detection device of the first embodiment. FIG. 7 describes the target substance detection device according to the second modified example.

As shown in FIG. 7, the target substance detection device 1B according to the second modified example includes a first magnetic field application unit 7 instead of the first magnetic field application unit 4 in the target substance detection device 1 of the first embodiment. This target substance detection device has a similar structure to the target substance detection device 1 according to the first embodiment in the other respects, and so the descriptions are omitted.

The first magnetic field application unit 7 includes an electromagnet, and is disposed obliquely upward of the detection region (the region on the rear face irradiated with light from the light irradiation unit 3 and generating the propagated light upward of the surface) on the surface of the liquid-sample introducing plate 2. The first magnetic field application unit 7 applies a magnetic field to move the conjugates in the liquid sample that are introduced to the surface of the liquid-sample introducing plate 2 in the direction having a vector component parallel to the in-plane direction of the surface of the liquid-sample introducing plate 2 (first conjugate moving step).

Figure 8:
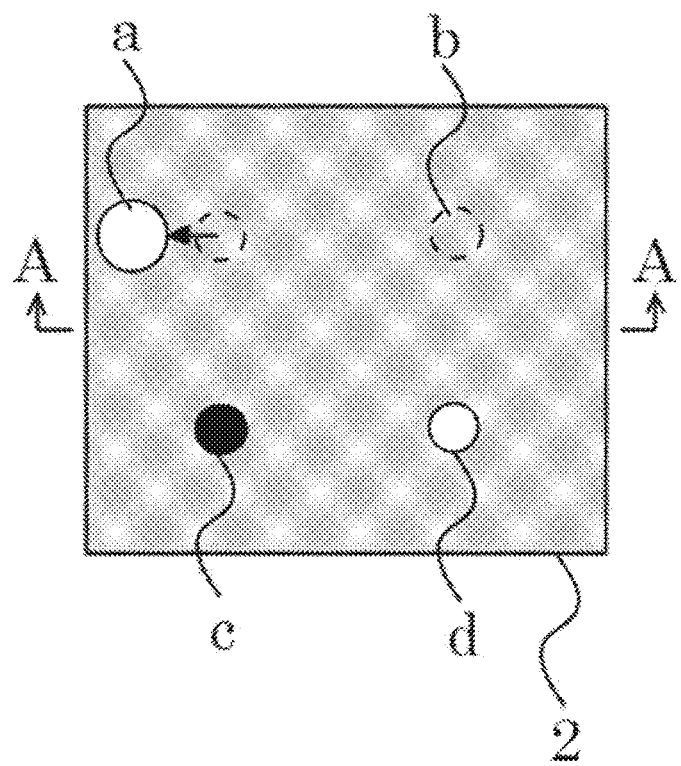
FIG. 8 is Drawing (2) schematically showing the surface of the liquid-sample introducing plate in the field of view that is observed with an imaging device after the conjugate moving step.

FIG. 8 schematically shows the surface of the liquid-sample introducing plate 2 in the field of view that is observed with the imaging device 5a after the first conjugate moving step implemented by the first magnetic field application unit 7. The surface of the liquid-sample introducing plate before the first conjugate moving step is similar to that in FIG. 2.

As is understood from a comparison between FIG. 2 showing the surface before the first conjugate moving step and FIG. 8 showing the surface after the first conjugate moving step, the optical signals a and b change between before and after the first conjugate moving step, and the optical signals c and d do not change between before and after the first conjugate moving step.

Similarly to the target substance detection device 1, the target substance detection device 1B therefore enables determination that the substances a' and b' generating the optical signals a and b include the target substance, and the optical signals c and d are noise signals due to scratches on the surface of the liquid-sample introducing plate 2, contaminants adsorbed to or present on the surface, fluctuation of the output from the light source and the like.

Figure 9:
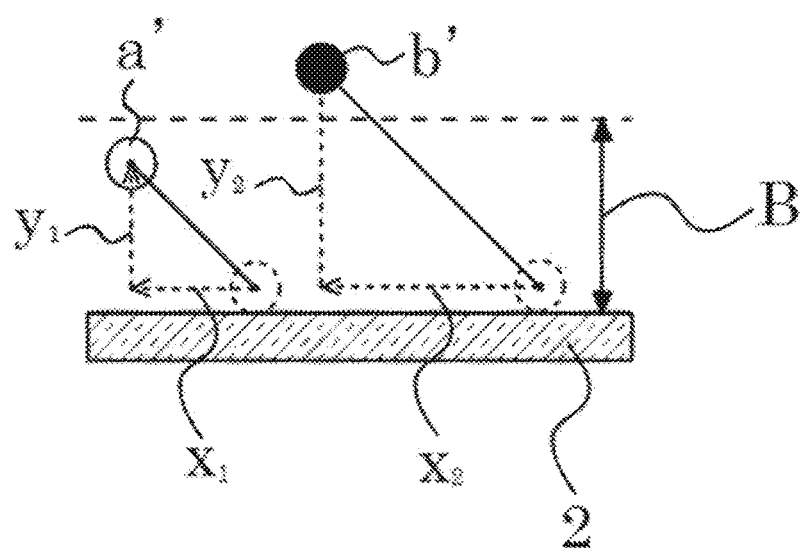
FIG. 9 is a cross-sectional view taken along the line A-A of FIG. 8.

FIG. 9 is a lateral view of the liquid-sample introducing plate 2 showing the substance a' that generates the optical signal a and the substance b' that generates the optical signal b after the first conjugate moving step implemented by the first magnetic field application unit 7. FIG. 9 is a cross-sectional view taken along the line A-A of FIG. 8. Arrow B in FIG. 9 indicates the imaging range where an optical signal can be obtained.

As shown in FIG. 9, the drawing magnetic field applied from the obliquely above by the first magnetic field application unit 7 moves the substance a' and the substance b' in the direction having vector components $x_1$ and $x_2$ parallel to the in-plane direction of the surface of the liquid-sample introducing plate 2 and in the direction having vector components $y_1$ and $y_2$ in the direction away from the liquid-sample introducing plate 2.

The target substance detection device 1B therefore is different from the target substance detection device 1, which moves the substance a' and the substance b' only in the direction away from the liquid-sample introducing plate 2, in the behavior after the first conjugate moving step.

Such a difference leads to a decrease in the burden to detect the target substance.

Specifically the following considers the case of detecting the target substance based on the optical signals a and b while comparing FIG. 4 and FIG. 8. FIGS. 4 and 8 are not different for the optical signal b because the optical signal b disappears in both of the cases. The optical signal a is different between FIG. 4 and FIG. 8. That is, FIG. 4 shows the detection of the target substance based on a change of the size, and this is not the case of the detection of the target substance based on the movement. FIG. 8 shows the detection of the target substance based on a change of the size as well as based on the movement of the optical signal, and so enables easier detection of the target substance than in FIG. 4.

In this way, the target substance detection device 1B enables more accurate detection of the target substance.

Second Embodiment

Figure 10:
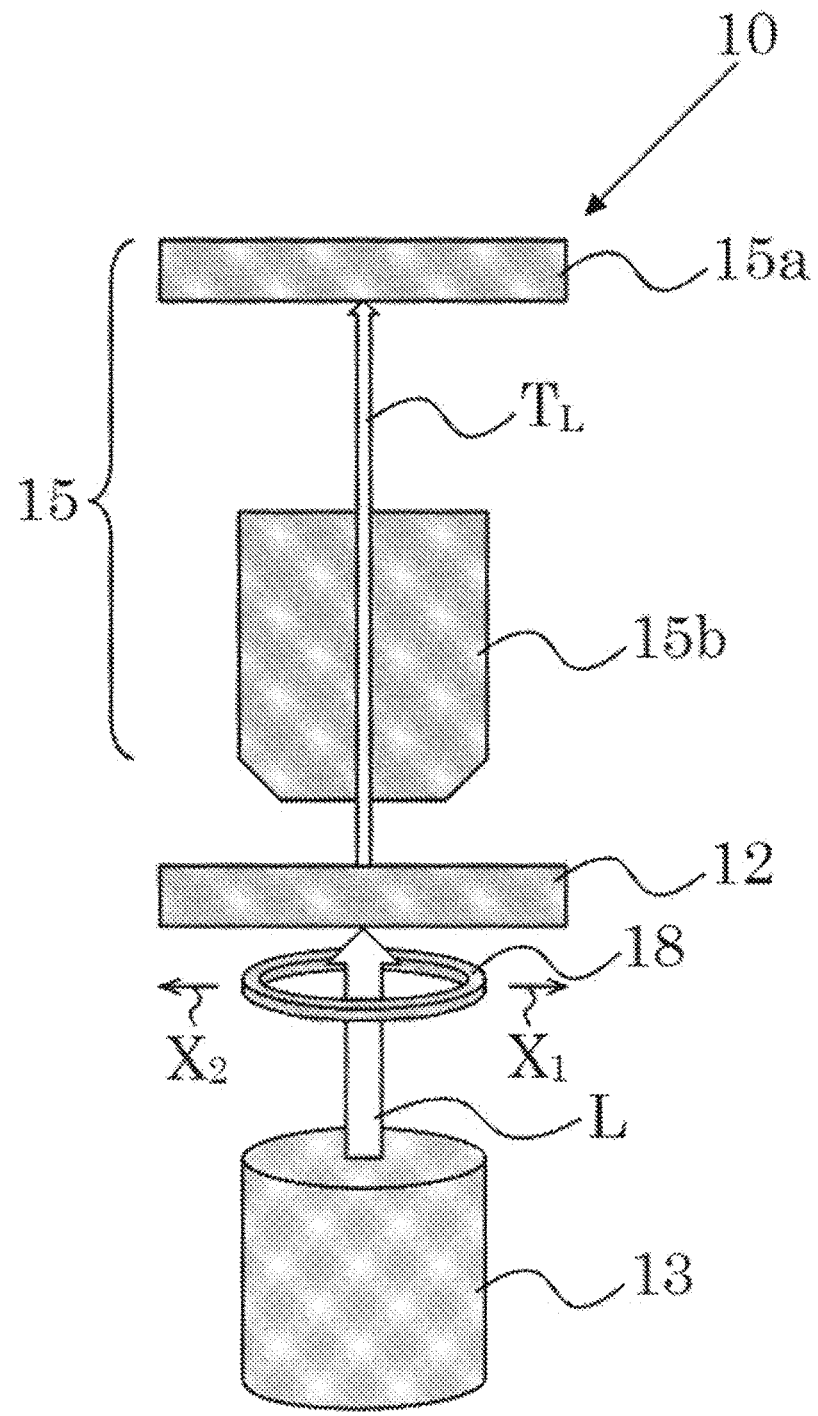
FIG. 10 describes a target substance detection device according to a second embodiment.

Next referring to FIG. 10, the following describes a target substance detection device according to a second embodiment of the present invention. FIG. 10 describes the target substance detection device according to the second embodiment.

As shown in FIG. 10, a target substance detection device 10 according to the second embodiment is configured like a well-known transmission type microscope, and includes a liquid-sample introducing plate 12, a light irradiation unit 13, a second magnetic field application unit 18, and an optical-signal detection unit 15 including an imaging device 15a and an objective lens 15b.

The liquid-sample introducing plate 12, the light irradiation unit 13, and the optical-signal detection unit 15 may be configured similarly to the liquid-sample introducing plate 2, the light irradiation unit 3 and the optical-signal detection unit 5 in the target substance detection device 1 according to the first embodiment. The target substance detection device 10 according to the second embodiment is different from the target substance detection device 1 according to the first embodiment in that it includes a second magnetic field application unit 18 instead of the first magnetic field application unit 4. The following describes a difference.

The second magnetic field application unit 18 is disposed on the side of the rear face of the liquid-sample introducing plate 12. The second magnetic field application unit 18 applies a magnetic field to draw the conjugates in the liquid sample that are introduced on the surface of the liquid-sample introducing plate 12 toward the surface of the liquid-sample introducing plate 12, and is movable in the direction having a vector component parallel to the in-plane direction of the surface of the liquid-sample introducing plate 12 while applying the magnetic field. The second magnetic field application unit 18 includes an annular permanent magnet having a through hole and a sliding member (not illustrated) that slides the permanent magnet in $X_1$ direction or in $X_2$ direction. The light irradiation unit 13 applies light to the liquid-sample introducing plate 12 from the rear face through the through hole.

The conjugates move as follows. The second magnetic field application unit 18 as the magnetic field application unit applies the magnetic field to draw the conjugates in the liquid sample introduced on the surface of the liquid-sample introducing plate 12 toward the surface of the liquid-sample introducing plate 12, and the second magnetic field application unit 18 moves in the direction having a vector component parallel to the in-plane direction of the surface of the liquid-sample introducing plate 12 while applying the magnetic field, so that the conjugates move while following the movement of the second magnetic field application unit 18 (second conjugate moving step).

Such a second magnetic field application unit 18 applies a magnetic field to draw all or a part of the conjugates in the liquid sample to the surface of the liquid-sample introducing plate 12 in the second conjugate moving step. This can save the time of waiting for the gravitational sedimentation of the conjugates floating in the liquid layer of the liquid sample on the surface of the liquid-sample introducing plate 12 after the liquid-sample introducing and holding step.

Figure 11:
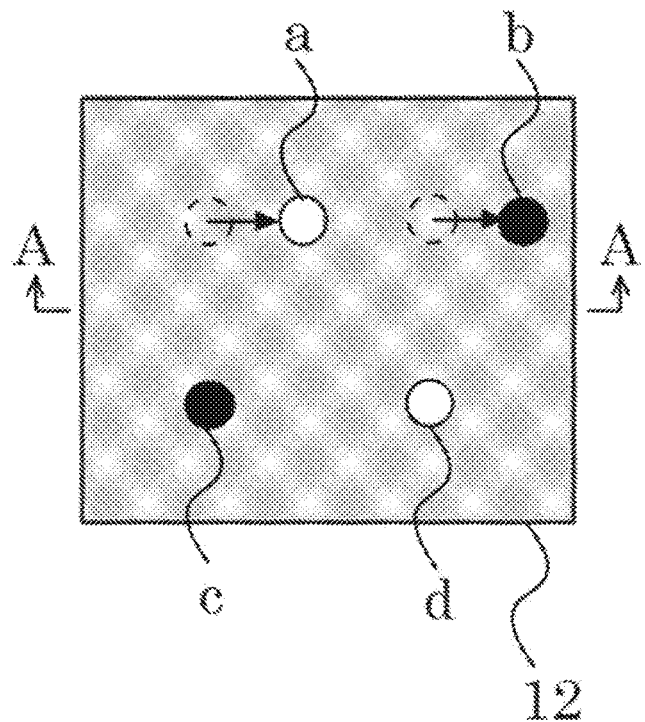
FIG. 11 is Drawing (3) schematically showing the surface of the liquid-sample introducing plate in the field of view that is observed with the imaging device after the conjugate moving step.
Figure 12:
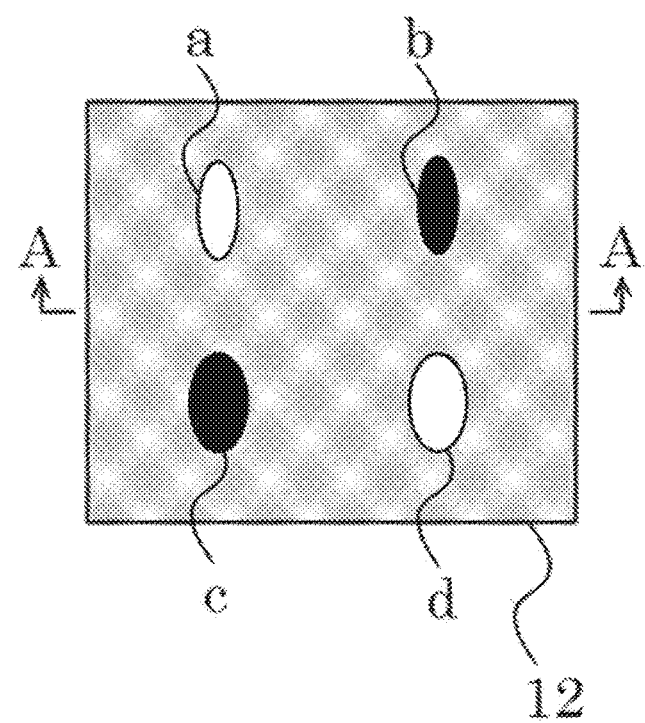
FIG. 12 is Drawing (2) schematically showing the surface of the liquid-sample introducing plate in the field of view that is observed with an imaging device.
Figure 13:
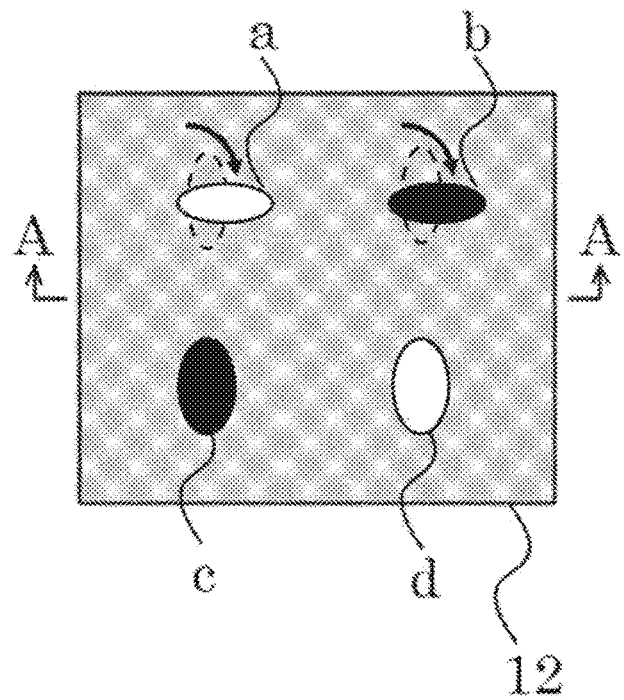
FIG. 13 is Drawing (4) schematically showing the surface of the liquid-sample introducing plate in the field of view that is observed with the imaging device after the conjugate moving step.

FIG. 11 schematically shows the surface of the liquid-sample introducing plate 12 in the field of view that is observed with the imaging device 15a after the second conjugate moving step. The surface of the liquid-sample introducing plate before the second conjugate moving step is similar to that in FIG. 2. FIG. 12 schematically shows the surface of the liquid-sample introducing plate before the second conjugate moving step, which shows the case where the optical signals have observable anisotropy. FIG. 13 schematically shows the surface of the liquid-sample introducing plate in this case and after the second conjugate moving step.

As is understood from a comparison between FIG. 2 and FIG. 11 showing the surface after the second conjugate moving step or a comparison between FIG. 12 and FIG. 13, the optical signals a and b change between before and after the second conjugate moving step, and the optical signals c and d do not change between before and after the second conjugate moving step.

The target substance detection device 10 therefore enables determination that the substances a' and b' generating the optical signals a and b include the target substance, and the optical signals c and d are noise signals due to scratches on the surface of the liquid-sample introducing plate 12, contaminants adsorbed to or present on the surface, fluctuation of the output from the light source and the like.

Figure 14:
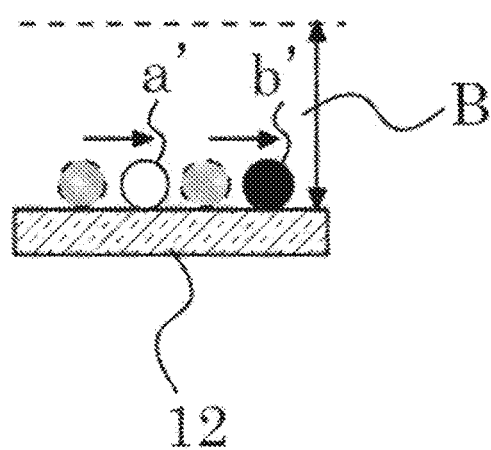
FIG. 14 is a cross-sectional view taken along the line A-A of FIG. 11.
Figure 15:
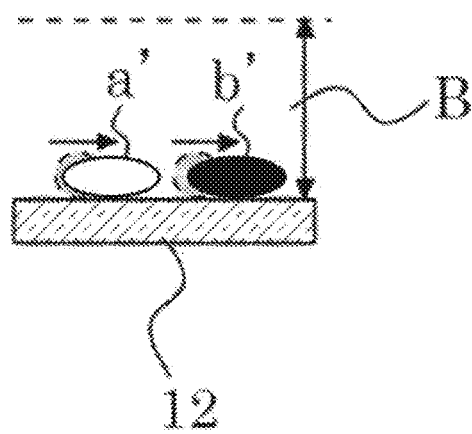
FIG. 15 is a cross-sectional view taken along the line A-A of FIG. 13.

FIG. 14 and FIG. 15 are lateral views of the liquid-sample introducing plate 12 showing the substance a' that generates the optical signal a and the substance b' that generates the optical signal b after the second conjugate moving step. FIG. 14 is a cross-sectional view taken along the line A-A of FIG. 11, and FIG. 15 is a cross-sectional view taken along the line A-A of FIG. 13. Arrow B in FIG. 14 and FIG. 15 indicates the imaging range where an optical signal can be obtained.

As shown in FIG. 14 and FIG. 15, the substance a' and the substance b' are firstly drawn to the surface of the liquid-sample introducing plate 12 by the magnetic field applied from the second magnetic field application unit 18. Then the substance a' and b' follow the movement of the second magnetic field application unit 18 in the direction having vector components parallel to the in-plane direction of the surface of the liquid-sample introducing plate 12 (direction $X_1$ or $X_2$ in FIG. 10), so as to move in the direction parallel to the in-plane direction of the liquid-sample introducing plate 12 or rotate.

FIG. 11 and FIG. 14 show the example of the movement of the substance a' and the substance b' in the field of view. In another example, when the movement of the second magnetic field application unit 18 is in the direction having vector components parallel to the in-plane direction of the surface of the liquid-sample introducing plate 12 and in the direction parallel to any one side of a rectangular field of view, and is longer than the one side, the substance a' and the substance b' are movable to the outside of the field of view. This enables accurate detection based on the disappearance of the optical signals a and b.

The target substance detection devices according to the first and the second embodiments have the optical system like a well-known upright microscope such that light is applied to the liquid-sample introducing plates 2 and 12 from the rear face and the optical-signal detection units 5 and 15 detect the optical signal based on the propagated light transmitted to the surface. The target substance detection device in another embodiment may be like a well-known inverted microscope such that light is applied to the liquid-sample introducing plate from the surface, and the optical-signal detection unit disposed on the side of the rear face detects the optical signal based on the propagated light transmitted to the rear face.

Third Embodiment

Figure 16:
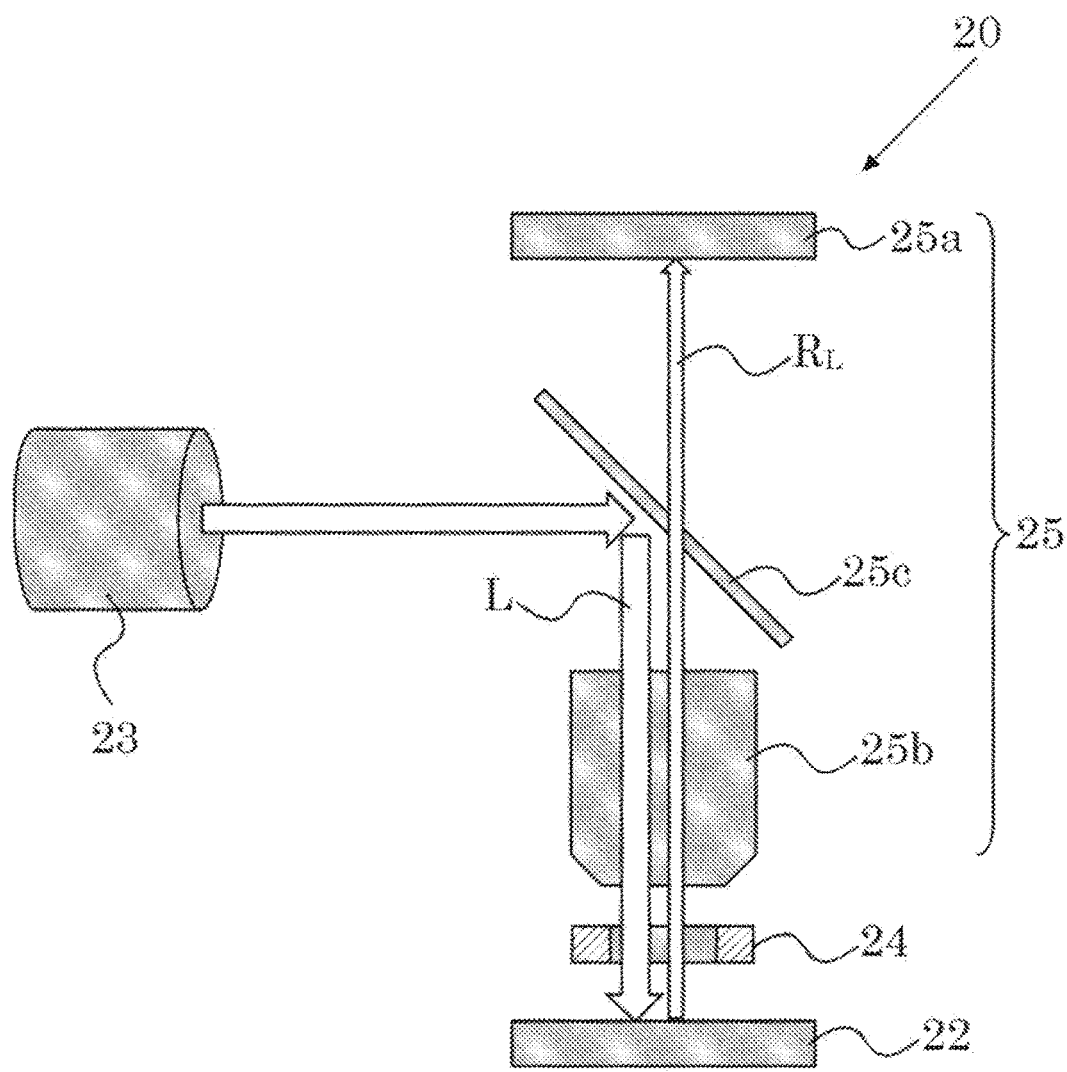
FIG. 16 describes a target substance detection device according to a third embodiment.

Next referring to FIG. 16, the following describes a target substance detection device according to a third embodiment of the present invention. FIG. 16 describes the target substance detection device according to the third embodiment.

As shown in FIG. 16, a target substance detection device 20 is configured like a well-known vertical illumination type microscope, and includes a liquid-sample introducing plate 22, a light irradiation unit 23, a first magnetic field application unit 24, and an optical-signal detection unit 25 including an imaging device 25a, an objective lens 25b, and a half mirror (e.g., dichroic mirror) 25c. In one example, the imaging device 25a includes a well-known CCD image sensor to acquire a two-dimensional image. The half mirror 25c operates as an optical element of the light irradiation unit 23 as well to reflect light and introduce the reflected light to the surface of the liquid-sample introducing plate 22.

The liquid-sample introducing plate 22 has a surface, to which a liquid sample is introduced. The liquid-sample introducing plate includes a reflective plate that reflects the light L irradiated from the surface and transmits the reflected light $R_L$ upward of the surface as propagated light. The liquid-sample introducing plate 22 itself makes up the liquid-sample holding unit, and after the liquid sample is introduced to the surface, a cover glass, for example, is placed so as to cover the liquid sample. In this way the liquid-sample introducing plate holds the liquid sample.

The light irradiation unit 23 makes up the surface light irradiation unit that applies the light L, which is the reflected light from the half mirror 25c, from the surface of the liquid-sample introducing plate 22.

The first magnetic field application unit 24 is disposed on the side of the surface of the liquid-sample introducing plate 22, and is configured to apply a magnetic field so as to move the conjugates in the liquid sample that are introduced onto the surface of the liquid-sample introducing plate 22 in the direction away from the liquid-sample introducing plate 22. The first magnetic field application unit 24 includes an annular electromagnet having a through hole at the center, and so the light L irradiated from the light irradiation unit 23 is applied to the liquid-sample introducing plate 22 via the through hole. The optical-signal detection unit 25 detects an optical signal based on the reflected light $R_L$ of the light L through the through hole.

The optical-signal detection unit 25 is disposed on the side of the surface of the liquid-sample introducing plate 22, and detects a change in optical signal based on the propagated light between before and after the application of the magnetic field by the first magnetic field application unit 24.

The liquid-sample introducing plate 22, the light irradiation unit 23 and the optical-signal detection unit 25 (imaging device 25a, the objective lens 25b, and the half mirror 25c) may be configured like a well-known vertical illumination type microscope.

Such a target substance detection device 20 firstly introduces a liquid sample to the surface of the liquid-sample introducing plate 22 and holds the liquid sample on the surface (liquid-sample introducing and holding step).

Next, after gravitational sedimentation of the conjugates floating in the liquid layer of the liquid sample on the surface of the liquid-sample introducing plate 22, the target substance detection device applies the light L from the light irradiation unit 23 to the surface of the liquid-sample introducing plate 22 via the half mirror 25c (light irradiation step), and adjusts the objective lens 25b so that the surface or the vicinity of the surface is within the imaging range to acquire an optical signal on the surface based on the reflected light $R_L$ of the light L with the imaging device 25a (optical-signal detection step).

Next the target substance detection device excites the electromagnet of the first magnetic field application unit 24 to apply a magnetic field to draw the conjugates in the liquid sample introduced to the surface of the liquid-sample introducing plate 22 toward the first magnetic field application unit 24, and move the conjugates in the direction away from the liquid-sample introducing plate 22 (first conjugate moving step).

Next, after moving the conjugates in the direction away from the liquid-sample introducing plate 22 while keeping the imaging range and the field of view, the target substance detection device acquires an optical signal on the surface of the liquid-sample introducing plate 22 with the imaging device 25a (optical-signal detection step).

Such a target substance detection device 20 obtains optical signals before and after the first conjugate moving step of the optical-signal detection step as shown in FIG. 2 and FIG. 4. This clearly distinguishes an optical signal based on the target substance from noise signals due to scratches on the surface of the liquid-sample introducing plate 22, contaminants adsorbed to or present on the surface, fluctuation of the output from the light source and the like.

In this way, the target substance detection device 20 enables accurate detection of the target substance. The target substance detection device allows detection of the target substance irrespective of contaminants adsorbed to the surface of the liquid-sample introducing plate 22, if any, and so does not require the washing process for the liquid-sample introducing plate 22 for every detection step. In this way the target substance detection device enables efficient detection. The target substance detection device deals with various types of optical signals that are generated based on scattered light, reflected light, light emission, and light absorption, as signals to be distinguished, and so will be applied in a wide range of fields. The target substance detection device deals with the phenomena of a change in optical signal including out-of-focus as well as disappearance of the optical signal, and so can obtain a change of the optical signal clearly.

Figure 17:
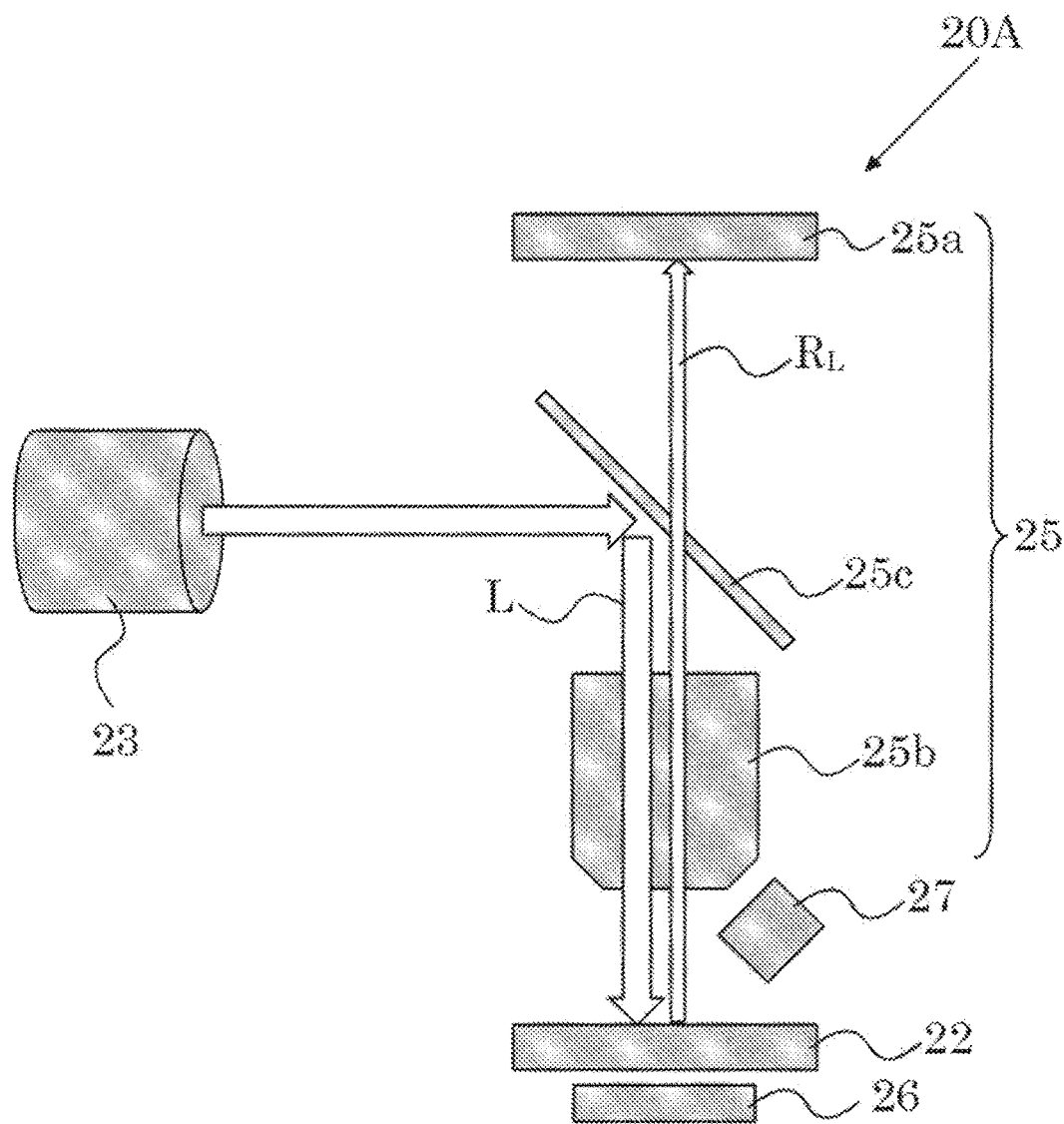
FIG. 17 describes a target substance detection device according to a modified example of the target substance detection device of the third embodiment.

Next referring to FIG. 17, the following describes a target substance detection device according to a modified example of the target substance detection device of the third embodiment. FIG. 17 describes the target substance detection device according to the modified example of the target substance detection device of the third embodiment.

As shown in FIG. 17, the target substance detection device 20A according to the modified example includes a third magnetic field application unit 26 in addition to the target substance detection device 20 of the third embodiment, and includes a first magnetic field application unit 27 instead of the first magnetic field application unit 24. This target substance detection device has a similar structure to the target substance detection device 20 according to the third embodiment in the other respects, and so the descriptions are omitted.

The third magnetic field application unit 26 includes an electromagnet and is disposed on the side of the rear face of the liquid-sample introducing plate 22. The third magnetic field application unit 26 is configured to apply a magnetic field so as to draw the conjugates in the liquid sample that are introduced to the liquid-sample introducing plate 22 toward the surface of the liquid-sample introducing plate 22.

Similarly to the target substance detection device 20, after the liquid-sample introducing and holding step and before the conjugate moving step, the third magnetic field application unit 26 applies a drawing magnetic field to draw the entire or a part of the conjugates in the liquid sample toward the surface of the liquid-sample introducing plate 22 without waiting for gravitational sedimentation of the floating conjugates in the liquid layer of the liquid sample on the surface of the liquid-sample introducing plate 22 (conjugate drawing step).

In addition to the advantageous effect of the target substance detection device 20, this target substance detection device 20A shortens the time required for the detection and so enables more efficient detection of the target substance.

The first magnetic field application unit 27 includes an electromagnet, and is disposed obliquely upward of the detection region (the region on the surface irradiated with light from the light irradiation unit 23 and generating the propagated light upward of the surface) on the surface of the liquid-sample introducing plate 22. The first magnetic field application unit 27 applies a magnetic field to move the conjugates in the liquid sample that are introduced to the surface of the liquid-sample introducing plate 22 in the direction having a vector component parallel to the in-plane direction of the surface of the liquid-sample introducing plate 22 (first conjugate moving step).

Such a target substance detection device 20A including the first magnetic field application unit 27 instead of the first magnetic field application unit 24 obtains optical signals before and after the first conjugate moving step of the optical-signal detection step as shown in FIG. 2 and FIG. 8. This enables detection of the target substance based on a change of the size of the optical signal a as well as based on the movement of the optical signal a as shown in FIG. 8, and so detects the target substance more accurately.

Fourth Embodiment

Figure 18:
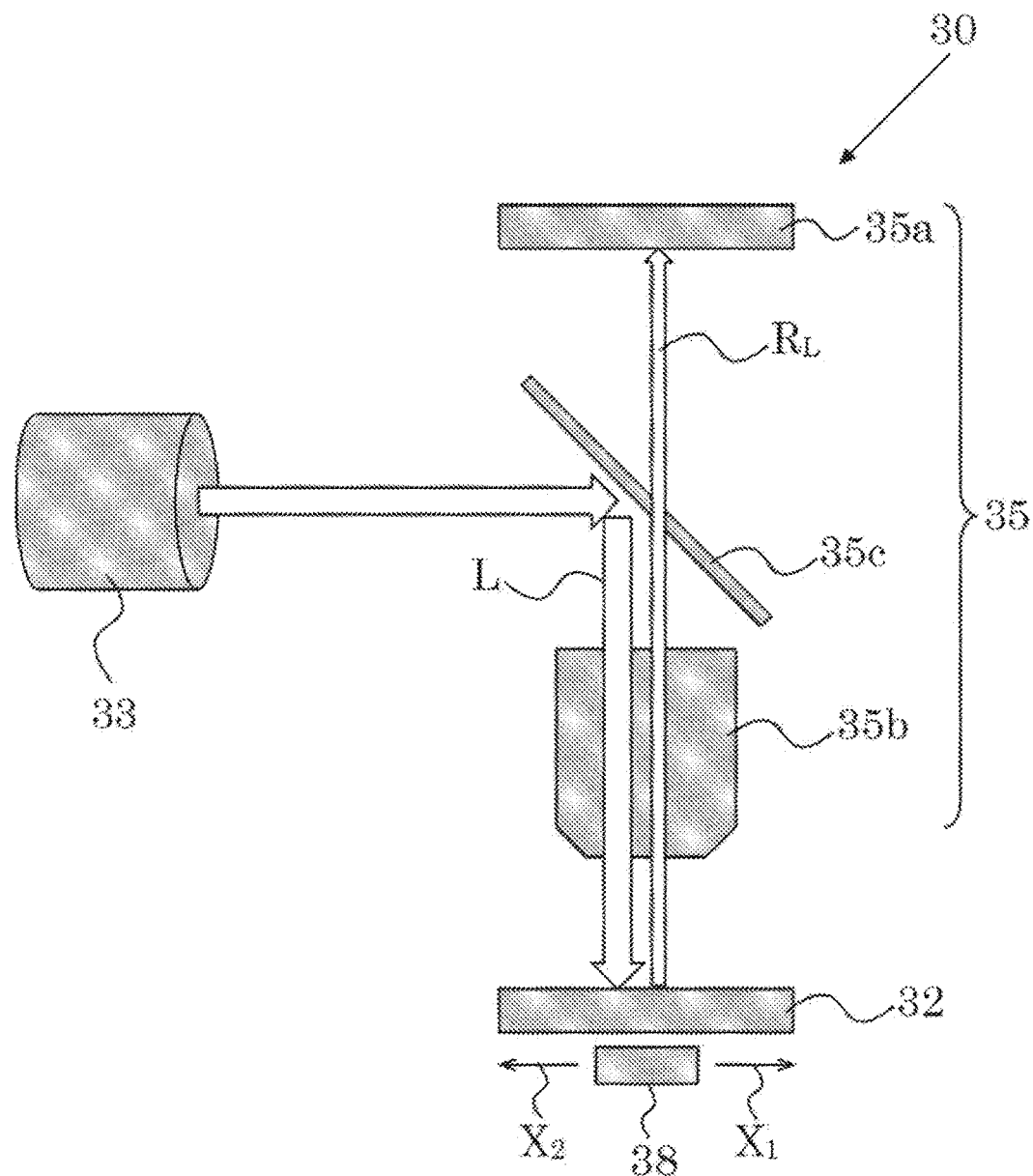
FIG. 18 describes a target substance detection device according to a fourth embodiment.

Next referring to FIG. 18, the following describes a target substance detection device according to a fourth embodiment of the present invention. FIG. 18 describes the target substance detection device according to the fourth embodiment.

As shown in FIG. 18, a target substance detection device 30 according to the fourth embodiment is configured like a well-known vertical illumination type microscope, and includes a liquid-sample introducing plate 32, a light irradiation unit 33, a second magnetic field application unit 38, and an optical-signal detection unit 35 including an imaging device 35a, an objective lens 35b and a half mirror 35c.

The liquid-sample introducing plate 32, the light irradiation unit 33, and the optical-signal detection unit 35 may be configured similarly to the liquid-sample introducing plate 22, the light irradiation unit 23 and the optical-signal detection unit 25 in the target substance detection device 20 according to the third embodiment. The target substance detection device 30 according to the fourth embodiment is different from the target substance detection device 20 according to the third embodiment in that it includes a second magnetic field application unit 38 instead of the first magnetic field application unit 24. The following describes a difference.

The second magnetic field application unit 38 is disposed on the side of the rear face of the liquid-sample introducing plate 32. The second magnetic field application unit 38 applies a magnetic field to draw the conjugates in the liquid sample that are introduced on the surface of the liquid-sample introducing plate 32 toward the surface of the liquid-sample introducing plate 32, and is movable in the direction having a vector component parallel to the in-plane direction of the surface of the liquid-sample introducing plate 32 while applying the magnetic field. The second magnetic field application unit 38 includes a permanent magnet and a sliding member (not illustrated) that slides the permanent magnet in $X_1$ direction or in $X_2$ direction.

The conjugates move as follows. The second magnetic field application unit 38 as the magnetic field application unit applies the magnetic field to draw the conjugates in the liquid sample introduced on the surface of the liquid-sample introducing plate 32 toward the surface of the liquid-sample introducing plate 32, and the second magnetic field application unit 38 moves in the direction having a vector component parallel to the in-plane direction of the surface of the liquid-sample introducing plate 32 while applying the magnetic field, so that the conjugates move while following the movement of the second magnetic field application unit 38 or change the orientation (second conjugate moving step).

Such second magnetic field application unit 38 applies a magnetic field to draw all or a part of the conjugates in the liquid sample to the surface of the liquid-sample introducing plate 32 in the second conjugate moving step. This can save the time of waiting for the gravitational sedimentation of the conjugates floating in the liquid layer of the liquid sample on the surface of the liquid-sample introducing plate 32 after the liquid-sample introducing and holding step.

Such a target substance detection device 30 obtains optical signals before and after the second conjugate moving step of the optical-signal detection step as shown in FIG. 2, FIG. 11, FIG. 12 and FIG. 13. This clearly distinguishes an optical signal based on the target substance from noise signals due to scratches on the surface of the liquid-sample introducing plate 32, contaminants adsorbed to or present on the surface, fluctuation of the output from the light source and the like.

FIG. 11 shows the example of the movement of the substance a' and the substance b' in the field of view. In another example, when the movement of the second magnetic field application unit 38 is in the direction having vector components parallel to the in-plane direction of the surface of the liquid-sample introducing plate 32 and in the direction parallel to any one side of a rectangular field of view, and is longer than the one side, the substance a' and the substance b' are movable to the outside of the field of view. This enables accurate detection based on the disappearance of the optical signals a and b.

The above describes the optical signals based on the conjugates that result from scattered light, reflected light and light emission by way of the examples of FIGS. 2, 4, 8, 11, 12 and 13. These examples are for the purpose of illustration, and the optical signals may result from transmitted light, such as phase difference and differential interference.

The above describes a change of the optical signals based on the conjugates, including the movement, out-of-focus, disappearance and rotation (orientation change of the conjugates) by way of the examples of FIGS. 4, 8, 11 and 13. Other examples of the change of the optical signals include an increase or decrease of the intensity (e.g., intensity decrease due to the out-of-focus), a phase change (phase change after the movement), and appearance (movement from the outside of the field of view).

The above embodiments include the light-transmissive plate or the reflective plate as the liquid-sample introducing plate. Another embodiment may include the introducing plate as the liquid-sample introducing plate. In this case, the target substance detection device includes the lateral face light irradiation unit as the light irradiation unit, and the optical-signal detection unit disposed on the side of the surface or the rear face of the liquid-sample introducing plate, so that the optical-signal detection unit detects scattered light, reflected light or the like from the conjugates. In another example, the optical-signal detection unit may be disposed on the side of the lateral face of the liquid-sample introducing plate (the lateral face on the opposite of the lateral face light irradiation unit of the liquid-sample introducing plate), and may detect light absorption, transmitted light or the like of the conjugates.

EXAMPLES

Example 1

Based on the configuration of the target substance detection device 1B of FIG. 7, a target substance detection device according to Example 1 was prepared as follows. For the purpose of illustration, the following describes the target substance detection device of Example 1 with the same reference numerals as those in the description of the target substance detection device 1B.

Specifically a board with grooves (manufactured by Memory-Tech Corporation, Thickness 0.6 mm, Groove pitch 1.2 μm) made of polycarbonate and having a $TiO_2$ thin film of 40 nm in thickness formed thereon was used as the liquid-sample introducing plate 2. A halogen lamp (manufactured by Olympus Corporation, 12V100WHAL) was used as the light irradiation unit 3, and a digital camera (manufactured by Olympus Corporation, DP21) was used as the imaging device 5a. A water-immersion type objective lens (manufactured by Olympus Corporation, WIMSPlanApo150x) was used as the objective lens 5b for observation while immersing the objective lens in the liquid sample on the surface of the liquid-sample introducing plate 2. A neodymium magnet (manufactured by As One Corporation, NR212) was used as the first magnetic field application unit 7. This magnet was brought closer to the liquid-sample introducing plate 2 during the observation to implement the conjugate moving step.

*Escherichia coli* was chosen for the target substance. The magnetic particles were obtained by reacting carboxyl group bearing magnetic labeled beads of 1 μm in diameter (manufactured by GE healthcare Corp. Sera-Mag Speedbeads) with the mixed liquid of N-hydroxysuccinimide and 1-ethyl-3-(3-dimethylaminopropyl) carbodiimide so as to substitute carboxyl group with active ester. These magnetic particles bind with amino groups on the surface of the *Escherichia coli*.

The solution containing the magnetic particles was mixed with the solution containing the target substance to prepare a mixed solution (liquid sample), and then 30 μl of this mixed solution was introduced between the liquid-sample introducing plate 2 and the objective lens 5b. The liquid-sample introducing plate 2 in this state was irradiated with the light from the light irradiation unit 3 to measure a transmitted-light signal with the imaging device 5a. To measure the transmitted-light signal, the focusing was obtained on the surface of the board using the grooves on the surface of the board.

Figure 19:
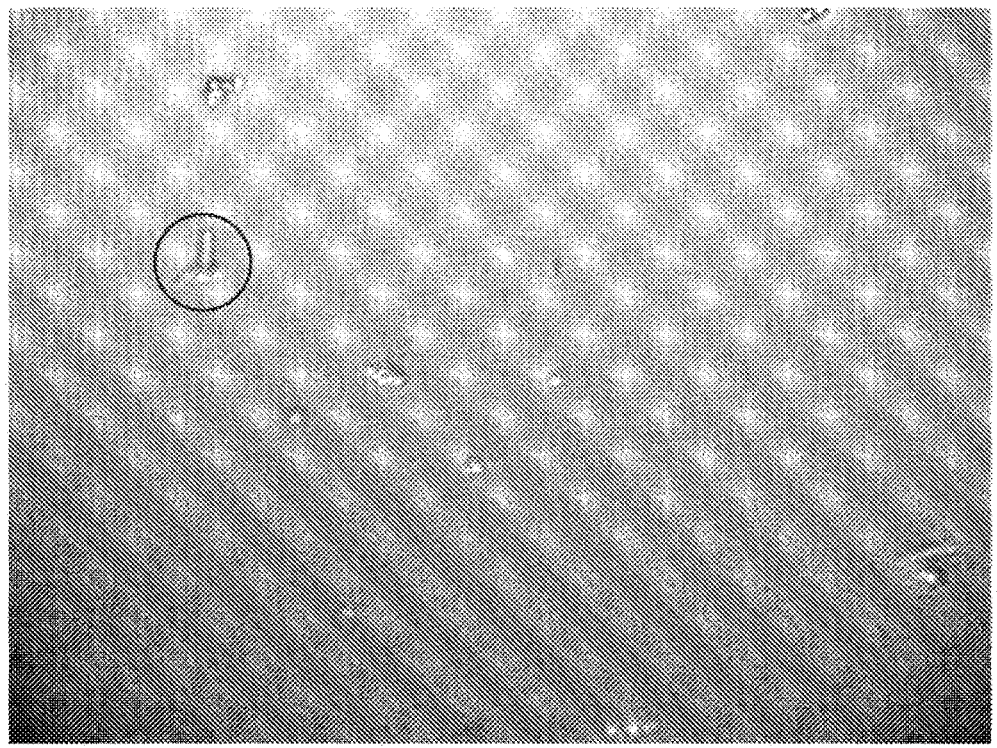
FIG. 19 shows a two-dimensional image before the application of the magnetic field in Example 1.

FIG. 19 shows an observed image when the application of a magnetic field started. FIG. 19 shows a two-dimensional image before the application of the magnetic field in Example 1.

In FIG. 19, the substance in the solid circle is a target substance bonding with a magnetic particle.

Figure 20:
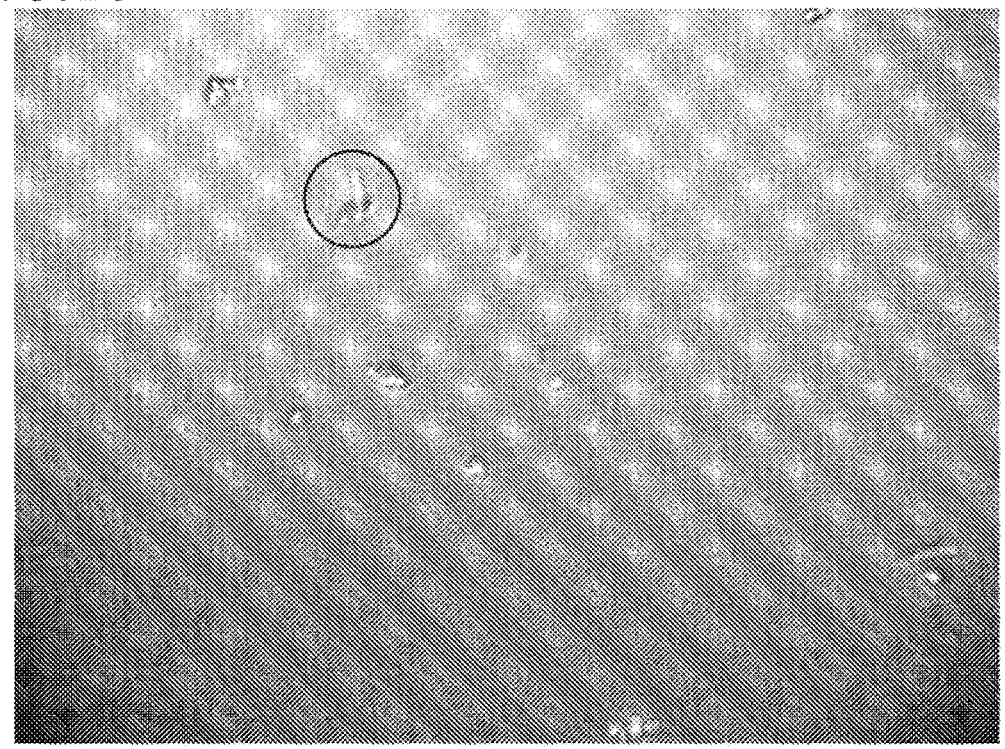
FIG. 20 shows a two-dimensional image after the application of the magnetic field in Example 1.

FIG. 20 shows an image observed after the first magnetic field application unit 7 applied a magnetic field in the direction drawing the conjugate from the right in FIG. 19. FIG. 20 shows a two-dimensional image after the application of the magnetic field in Example 1. FIG. 19 and FIG. 20 show two-dimensional images taken in the same field of view.

The substance in the solid circle in FIG. 20 is identical with the substance in the solid circle in FIG. 19. These drawings clearly show that the conjugate moved in the direction of the applied magnetic field over time after the starting of the application of the magnetic field.

Example 2

Based on the configuration of the target substance detection device 30 of FIG. 18, a target substance detection device according to Example 2 was prepared as follows. For the purpose of illustration, the following describes the target substance detection device of Example 2 with the same reference numerals as those in the description of the target substance detection device 30.

Specifically a board with grooves (manufactured by Memory-Tech Corporation, Thickness 0.6 mm, Groove pitch 1.2 μm) made of polycarbonate and having a $TiO_2$ thin film of 40 nm in thickness formed thereon was used as the liquid-sample introducing plate 32. A xenon lamp (manufactured by Olympus Corporation, UXL-75XB) was used as the light irradiation unit 33, and a digital camera (manufactured by Olympus Corporation, DP21) was used as the imaging device 35a. A half mirror 35c as a set of an optical filter (manufactured by Opto-line Inc. LF405/LP-B) was used to irradiate the liquid-sample introducing plate 32 with the light of 370 nm to 410 nm in wavelength. The light having a wavelength longer than 422 nm then was observed with the imaging device 35a. A ring-shaped neodymium magnet (manufactured by As One Corporation, NR212) was used as the second magnetic field application unit 38. This magnet was placed directly below an objective lens 35b (manufactured by Olympus Corporation, LMPlanF150x).

Similarly to Example 1, *Escherichia coli* was chosen for the target substance. Similarly to Example 1, the magnetic particles were obtained by reacting carboxyl group bearing magnetic labeled beads of 1 μm in diameter with the mixed liquid of N-hydroxysuccinimide and 1-ethyl-3-(3-dimethylaminopropyl) carbodiimide so as to substitute carboxyl group with active ester.

The solution containing these magnetic particles was mixed with the solution containing the target substance, and the solution containing fluorescent dye 4',6-diamidino-2-phenylindole (DAPI) also was mixed to the solution to prepare a mixed solution (liquid sample).

Drops of 10 μL of this mixed solution were placed on the liquid-sample introducing plate 32. The liquid-sample introducing plate 32 in this state was irradiated with the light from the light irradiation unit 33 to measure a fluorescent signal with the imaging device 35a.

Figure 21:
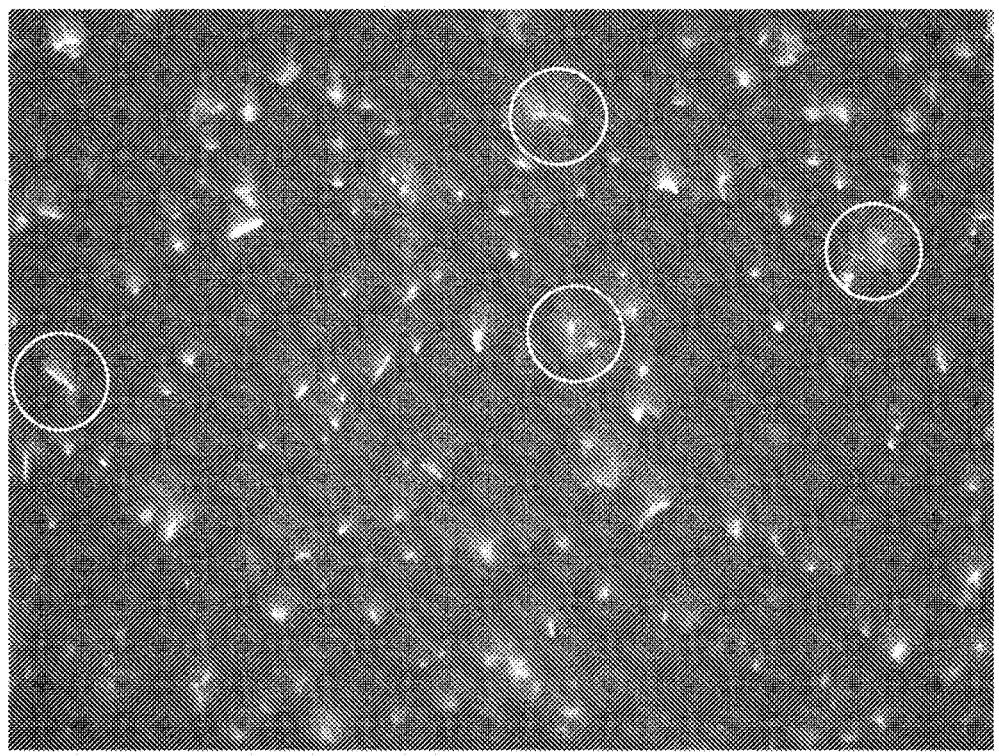
FIG. 21 shows a two-dimensional image before the movement of the magnetic field application unit in Example 2.

FIG. 21 shows an observed image after a certain time has passed after the dropping of the mixed solution. FIG. 21 shows a two-dimensional image before the movement of the magnetic field application unit in Example 2.

White parts in FIG. 21 mainly show fluorescence from the target substance that was labeled with the fluorescent dye.

Figure 22:
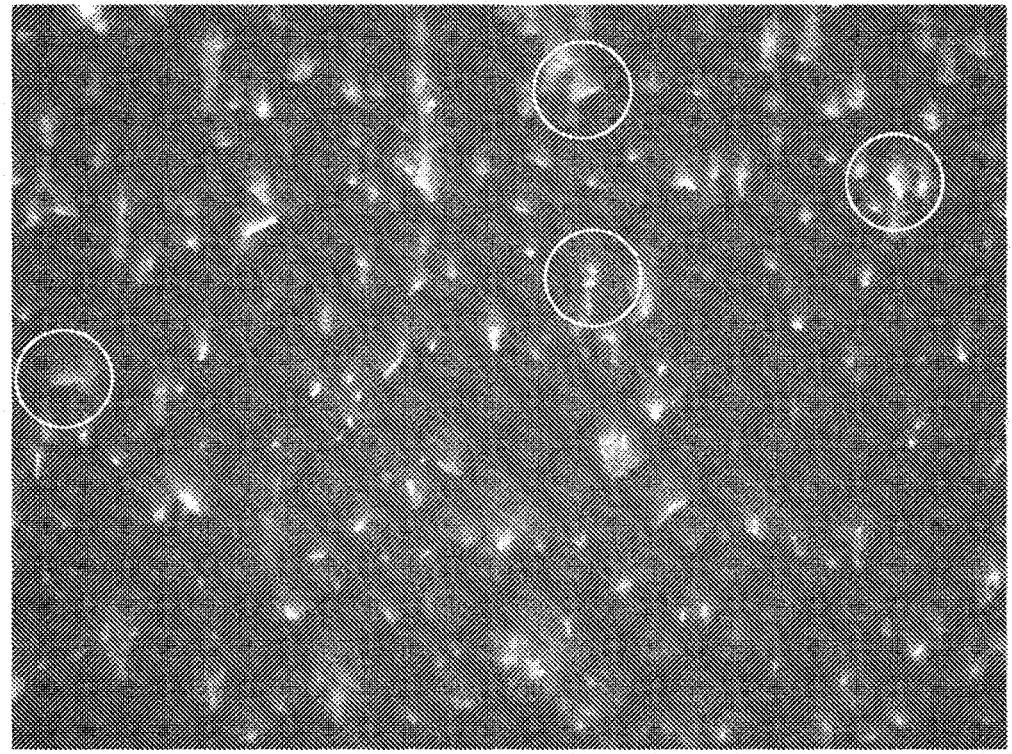
FIG. 22 shows a two-dimensional image after the movement of the magnetic field application unit in Example 2.

FIG. 22 shows an image observed after the second magnetic field application unit 38 moved downward in FIG. 21. FIG. 22 shows a two-dimensional image after the movement of the magnetic field application unit in Example 2.

As shown in FIG. 21 and FIG. 22, a part of the magnetic particles moved following the movement of the second magnetic field application unit 38, and the target substance bonding with the magnetic particles was different in the light emission of fluorescence. More specifically, such a difference results from a change of the light-emission position due to the parallel movement or the rotation of the target substance or a change in the light-emission intensity of the target substance due to the movement of the magnetic particles or the target substance.

Such a change was notably observable at the parts in the solid circles in FIG. 21 and FIG. 22.

DESCRIPTION OF REFERENCE NUMERALS 1, 1A, 1B, 10, 20, 20A, 30 target substance detection device
2, 12, 22, 32 liquid-sample introducing plate
3, 13, 23, 33 light irradiation unit
4, 7, 24, 27 first magnetic field application unit
5a, 15a, 25a, 35a imaging device
5b, 15b, 25b, 35b objective lens
25c, 35c half mirror
5, 15, 25, 35 optical-signal detection unit
6, 26 third magnetic field application unit
18, 38 second magnetic field application unit
L light
$T_L$ transmitted light
$R_L$ reflected light
a, b, c, d optical signal
a', b' substance
$X_1$, $X_2$ direction
$x_1$, $x_2$, $y_1$, $y_2$ vector component.

The invention claimed is:

1. A target substance detection device comprising:
a liquid-sample holding unit that comprises a plate on which is a liquid sample including a target substance and a magnetic particle that form a conjugate;
a light-irradiation unit configured to irradiate the liquid sample on the plate with propagated light;
a magnetic field application unit configured to apply magnetic field to the liquid sample on the plate in a manner that the applied magnetic field changes in a period of time; and
an optical-signal detection unit configured to receive an optical signal from the liquid sample generated as a result of the irradiation before and after the applied magnetic field changes,
wherein
the optical-signal detection unit is further configured to determine that the optical signal is from the conjugate when the optical signal changes between before and after the applied magnetic field changes, and
a surface of the plate is surface-treated with adsorption inhibitor that inhibits adsorption of the conjugate.

2. The target substance detection device according to claim 1, wherein
the optical-signal detection unit is further configured to determine that the optical signal of the substance is not the conjugate when the optical signal does not change between before and after the applied magnetic field changes.

3. The target substance detection device according to claim 1, wherein the optical-signal detection unit enables acquisition of an image of a detection region on the surface of the liquid-sample introducing plate as a two-dimensional image.

4. A target substance detection method using the target substance detection device according to claim 1 comprising:
irradiating, by the light irradiating unit, the light onto the plate;
applying, by the magnetic field application unit, the magnetic field onto the plate;
receiving, by the optical-signal detection unit, the light from the plate before and after the applying the magnetic field onto the plate; and
determining, by the optical-signal detection unit, that the optical signal of the substance represents the conjugate:
(1) when the optical signal changes between an optical signal of the substance detected before the magnetic field is applied and an optical signal of the substance detected after the magnetic field is applied; or
(2) when the optical signal of the substance is detected before the magnetic field is applied and the optical signal of the substance is not detected after the magnetic field is applied.

5. The target substance detection method according to claim 4 further comprising:
determining, by the optical-signal detection unit, that the optical signal of the substance is not the conjugate when the optical signal does not change between an optical signal of the substance detected before the magnetic field is applied and an optical signal of the substance detected after the magnetic field is applied.

* * * * *